United States Patent
Abbott et al.

(10) Patent No.: US 12,285,301 B2
(45) Date of Patent: Apr. 29, 2025

(54) MODULAR CLAMPS FOR MOUNTING SURGICAL MANIPULATORS

(71) Applicant: INTUITIVE SURGICAL OPERATIONS, INC., Sunnyvale, CA (US)

(72) Inventors: Ryan C. Abbott, San Jose, CA (US); Daniel H. Gomez, Los Gatos, CA (US); John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 705 days.

(21) Appl. No.: 17/444,158

(22) Filed: Jul. 30, 2021

(65) Prior Publication Data

US 2022/0039909 A1 Feb. 10, 2022

Related U.S. Application Data

(60) Provisional application No. 63/063,181, filed on Aug. 7, 2020.

(51) Int. Cl.
| | |
|---|---|
| A61B 90/57 | (2016.01) |
| A61B 34/00 | (2016.01) |
| A61B 90/35 | (2016.01) |

(52) U.S. Cl.
CPC .............. *A61B 90/57* (2016.02); *A61B 34/70* (2016.02); *A61B 90/35* (2016.02); *A61B 2090/571* (2016.02)

(58) Field of Classification Search
CPC ......... A61B 90/57; A61B 90/35; A61B 34/70; A61B 2090/571
See application file for complete search history.

(56) References Cited

U.S. PATENT DOCUMENTS

| 6,622,980 B2 * | 9/2003 | Boucher | F16B 7/0493 |
| | | | 248/231.51 |
| 9,107,784 B2 * | 8/2015 | Doyle | F16B 2/185 |
| 10,478,363 B2 * | 11/2019 | Koch | A61G 13/101 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Anita M King
(74) *Attorney, Agent, or Firm* — JONES ROBB, PLLC

(57) ABSTRACT

A system generally includes a surgical manipulator configured to control motion of a surgical tool, and a clamping apparatus having a mounting location configured to support the surgical manipulator and couple to a mounting structure. The clamping apparatus may include a body, a first jaw coupled to the body and configured to engage a first portion of the mounting structure, and a second jaw coupled to the body and configured to engage a second portion of the mounting structure. At least one of the first jaw and the second jaw may be movably coupled to the body and configured to move along a non-linear path to clamp mounting structures of different sizes. A lever may be pivotably coupled to the body and may be movable between a unclamped position and a clamped position. Alternatively, a motor may be operable to attach the clamping apparatus to the mounting structure.

22 Claims, 17 Drawing Sheets

(56) References Cited

U.S. PATENT DOCUMENTS

| | | | | |
|---|---|---|---|---|
| 10,814,501 B2* | 10/2020 | Auld | ............... | A61B 34/30 |
| 11,248,634 B2* | 2/2022 | Shetty | ............... | F16B 2/10 |
| 11,717,459 B2* | 8/2023 | Kovacs | ............... | A61B 90/57 |
| | | | | 248/229.22 |
| 2006/0290076 A1* | 12/2006 | Lees | ............... | A61G 13/101 |
| | | | | 279/44 |
| 2016/0296401 A1* | 10/2016 | Cole | ............... | A61F 5/3776 |
| 2021/0137635 A1* | 5/2021 | Gomez | ............... | B25J 9/0009 |

* cited by examiner

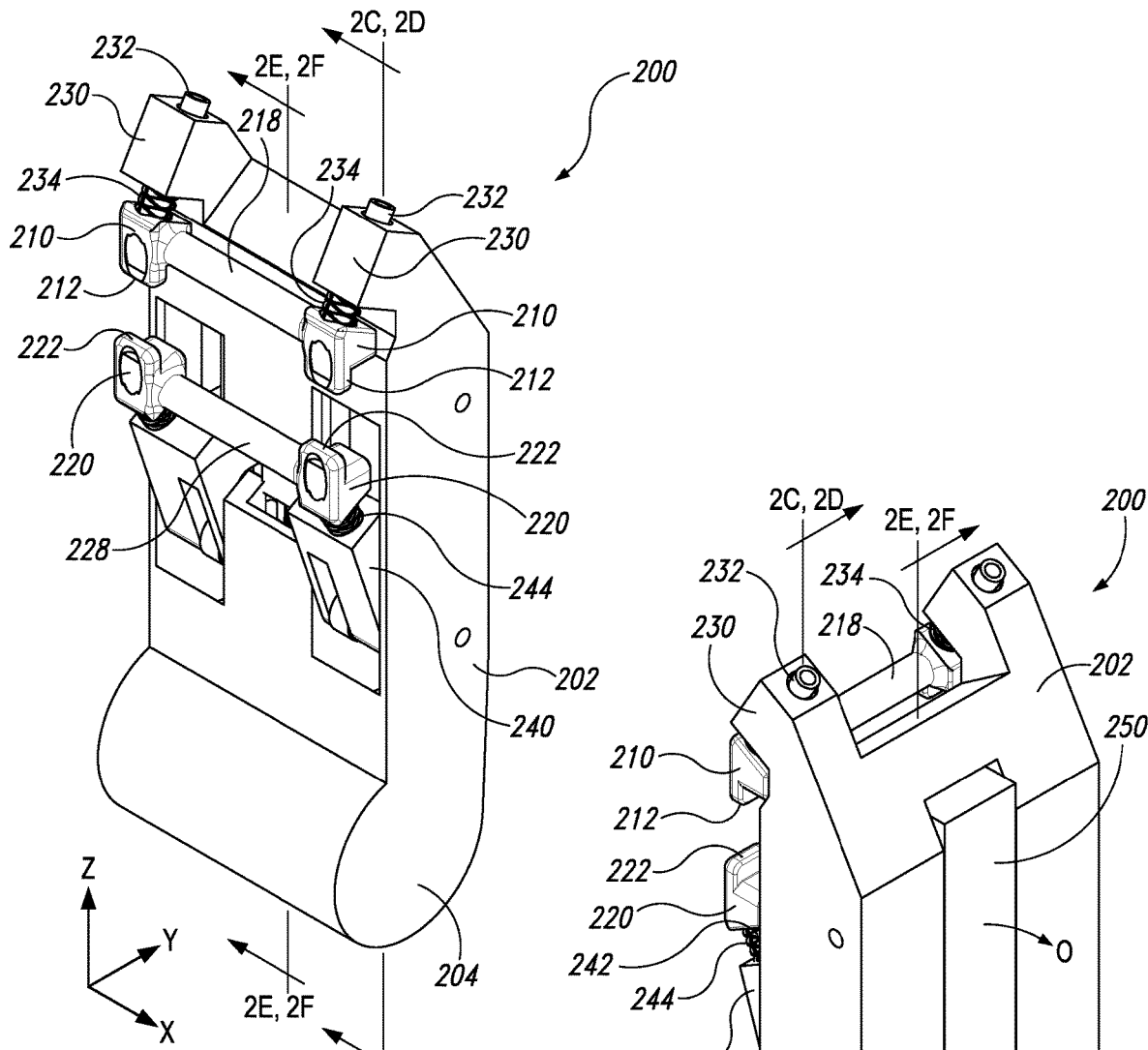
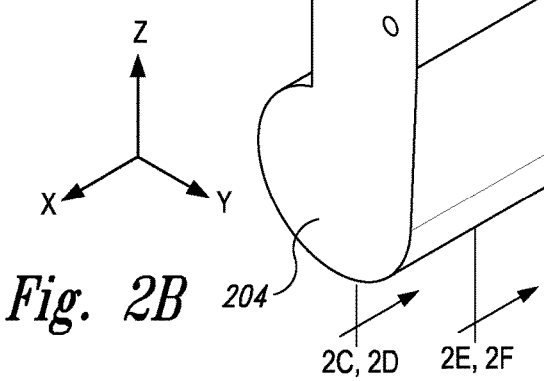
Fig. 2A
Fig. 2B

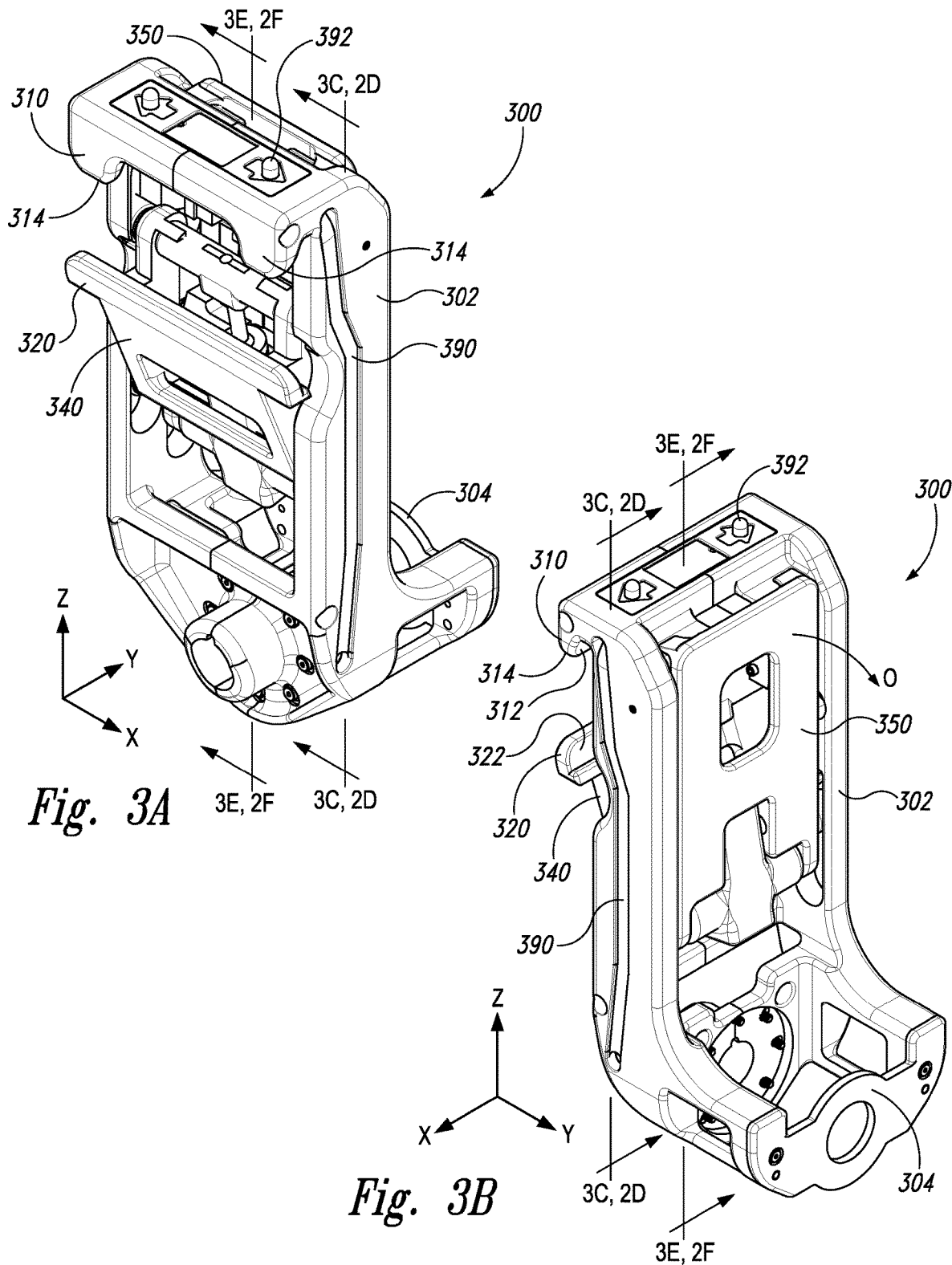

MODULAR CLAMPS FOR MOUNTING SURGICAL MANIPULATORS

CROSS REFERENCE TO RELATED APPLICATION

This application claims the benefit under 35 U.S.C. § 119(e) of U.S. Provisional Application No. 63/063,181, filed Aug. 7, 2020, entitled "Modular Clamps For Mounting Surgical Manipulators," which is hereby incorporated by reference for all purposes in its entirety.

TECHNICAL FIELD

Aspects of the present disclosure generally relate to devices and methods for performing a computer-assisted teleoperated procedure and, more specifically, to devices for arranging and mounting various tools for the computer-assisted teleoperated procedure.

BACKGROUND

Minimally invasive medical techniques are intended to reduce an amount of tissue that is damaged during medical procedures, thereby reducing patient recovery time, discomfort, and harmful side effects. Such minimally invasive techniques may be performed through natural orifices in a patient anatomy or through one or more surgical incisions. An operator (e.g., a physician) may insert minimally invasive medical instruments (surgical, diagnostic, therapeutic, biopsy instruments, etc.) through these natural orifices or incisions to reach a target tissue location. Robotic medical systems allow a user to control such medical instruments via a manipulator to which the instrument is mounted. One such minimally invasive technique is to mount a modular manipulator assembly to a surgical table with a clamp and independently move one or more instruments to a region of interest within the patient anatomy to perform a medical procedure. Control of such a manipulator assembly by an operator involves the management of several degrees of freedom including at least the management of insertion, retraction, and roll of the instrument with respect to the patient anatomy, as well as articulation of an instrument end effector.

Modular systems can use arrangeable clamps to mount various tools to a mounting structure. Manufacturers of systems having modular equipment mounting structures (e.g., operating tables, side carts, etc.) may specify their mounting structures with differing dimensions, which requires the arrangeable clamps to have corresponding features to accommodate the particular configuration of the mounting structure. In practice, a procurement order for a modular system using arrangeable clamps must specify the dimensions of the mounting structure (e.g., the height and width of a mounting rail), and consequently, the modular system is not usable with other mounting structures having dimensions the arrangeable clamps cannot accommodate.

SUMMARY

In accordance with embodiments of the present disclosure, a clamping apparatus is provided to support a robotic manipulator and couple to mounting structures of different sizes (e.g., structures having different heights, widths, and/or depths). The clamping apparatus has one or more jaws configured to move along a nonlinear path to accommodate different rail sizes.

In accordance with an embodiment of the present disclosure, a system is provided. The system generally includes a surgical manipulator configured to control motion of a surgical tool, and a clamping apparatus having a mounting location configured to support the surgical manipulator and couple to a mounting structure. The clamping apparatus may include a body, a first jaw coupled to the body and configured to engage a first portion of the mounting structure, and a second jaw coupled to the body and configured to engage a second portion of the mounting structure. At least one of the first jaw and the second jaw may be movably coupled to the body and configured to move along a non-linear path to clamp mounting structures of different sizes.

In accordance with an embodiment of the present disclosure, a clamping apparatus is provided. The clamping apparatus generally includes a body having a first cam slot having a non-linear path and a second cam slot, a first jaw fixed to the body and configured to engage a portion of a mounting structure, and a second jaw movably coupled to the body within the first and second cam slots. The clamping apparatus may further include a lever pivotably coupled to the body and the second jaw and movable between a first position, wherein the clamping apparatus has an unclamped mechanical state, to a second position, wherein the clamping apparatus has a clamped mechanical state, wherein articulation of the lever away from the first position toward the second position may cause the second jaw to move within the first and second cam slots toward the first jaw, and wherein the non-linear path of the first cam slot may initially cause the second jaw to move outwardly away from the body as the second jaw moves toward the first jaw. The clamping apparatus may further include a biasing member positioned between the body and the lever and configured to bias the second jaw against the mounting structure in the first position, wherein articulation of the lever toward the second position after the second jaw contacts the mounting structure may cause the biasing member to compress along a compliance direction.

In accordance with an embodiment of the present disclosure, a clamping apparatus is provided. The clamping apparatus generally includes a body, a first jaw fixed to the body and configured to engage a portion of a mounting structure, an articulable bracket movably coupled to the body, and a second jaw movably coupled to the articulable bracket. The clamping apparatus may further include a lever pivotably coupled to the body and the second jaw and movable between a first position, wherein the clamping apparatus is unclamped, to a second position, wherein the clamping apparatus is clamped, wherein articulation of the lever away from the first position toward the second position may cause the second jaw to move toward the first jaw. The clamping apparatus may further include a first biasing member positioned between the body and the lever and configured to bias the lever toward the first position, wherein articulation of the lever toward the second position after the second jaw contacts the mounting structure may cause the first biasing member to compress along a first compliance direction. The clamping apparatus may further include a second biasing member positioned between the articulable bracket and the second jaw and configured to bias the second jaw away from the articulable bracket, wherein articulation of the lever toward the second position after the second jaw contacts the mounting structure may causes the second biasing member to compress along a second compliance direction.

In accordance with an embodiment of the present disclosure, a clamping apparatus is provided. The clamping apparatus generally includes a first jaw fixed to a body and configured to engage a portion of a mounting structure, a second jaw movably coupled to the body and having an angled surface to accommodate a range of widths of the mounting structure, and a motor operably coupled to the body and the second jaw to move the second jaw between a first position, wherein the clamping apparatus has an unclamped mechanical state, and a second position, wherein the clamping apparatus has a clamped mechanical state, wherein actuation of the motor in the first position may cause the second jaw to move toward the first jaw. The clamping apparatus may further include a sensor configured to detect the mounting structure, wherein the motor may be operable when the sensor detects the mounting structure.

In accordance with an embodiment of the present disclosure, a clamping apparatus is provided. The clamping apparatus generally includes a body, a first jaw slidingly coupled to the body and having a first surface configured engage an upper portion of a mounting structure and a second surface configured to engage a lateral portion of the mounting structure, a second jaw movably coupled to the body and having a third surface configured engage a lower portion of the mounting structure and a fourth surface configured to engage the lateral portion of the mounting structure engaged by the first surface of the first jaw, and a motor operably coupled to the body and the second jaw to move the second jaw between a first position, wherein the clamping apparatus is unclamped, and a second position, wherein the clamping apparatus is clamped, wherein actuation of the motor in the first position may cause the second jaw to move toward the first jaw. The clamping apparatus may further include a sensor configured to detect the mounting structure, wherein the motor may be operable when the sensor detects the mounting structure.

In accordance with any of the embodiments disclosed herein, the movement of the second jaw may be arcuate.

In accordance with any of the embodiments disclosed herein, the mounting structure may comprise a rail, and wherein the first jaw may be configured to abut an upper portion of the rail and the second jaw may be configured to abut a lower portion of the rail when the clamping apparatus is clamped to the rail.

In accordance with any of the embodiments disclosed herein, the non-linear path of the first cam slot may be configured to move the second jaw inwardly toward the rail as the second jaw moves toward the first jaw after the first cam slot initially causes the second jaw to move outwardly away from the body.

In accordance with any of the embodiments disclosed herein, the movement of the second jaw within the first and second cam slots may be locked when the lever is in the second position.

In accordance with any of the embodiments disclosed herein, the movement of the second jaw within the first and second cam slots may be locked by a toothed interface between the lever and the body, fixing the biasing member in the compliance direction.

In accordance with any of the embodiments disclosed herein, the biasing member may be a first biasing member and the compliance direction is a first compliance direction, the clamping apparatus may further comprise an articulable bracket positioned between the second jaw and the body and configured to allow movement of the second jaw in a second compliance direction independent of the movement within the first and second cam slots, and the movement of the second jaw with respect to the articulable bracket may be biased by a second biasing member.

In accordance with any of the embodiments disclosed herein, the movement of the second jaw with respect to the articulable bracket may be locked when the lever is in the second position.

In accordance with any of the embodiments disclosed herein, the movement of the second jaw with respect to the articulable bracket may be locked by a toothed arm interfacing with the second jaw, fixing the second biasing member in the second compliance direction.

In accordance with any of the embodiments disclosed herein, the first jaw may have an angled surface to accommodate a range of widths of the mounting structure.

In accordance with any of the embodiments disclosed herein, the lever may be retained in the second position by an over-center configuration.

In accordance with any of the embodiments disclosed herein, the lever may have an articulable portion that interfaces with the body to retain the lever in the second position until the articulable portion is rotated.

In accordance with any of the embodiments disclosed herein, one or more of the first jaw and second jaw may have rounded edges to reduce abrasion of a drape positioned between the clamping apparatus and the mounting structure.

In accordance with any of the embodiments disclosed herein, the body may further comprise a mounting feature configured to receive a component and releasably couple the component to the clamping apparatus.

In accordance with any of the embodiments disclosed herein, the body may further comprise a cable receptacle configured to receive a cable therein.

In accordance with any of the embodiments disclosed herein, the body may further comprise a connector cavity at an end of the cable receptacle to receive a connector therein.

In accordance with any of the embodiments disclosed herein, the apparatus may further comprise a sensor configured to detect load on the clamping apparatus to signal an improper connection.

In accordance with any of the embodiments disclosed herein, the apparatus may further comprise a lamp configured to illuminate when the clamping apparatus is properly clamped to the mounting structure In accordance with any of the embodiments disclosed herein, the sensor may be a first sensor, and wherein the clamping apparatus may further comprise a second sensor configured to stop actuation of the motor when the second and fourth surfaces contact the lateral portion of the mounting structure.

In accordance with any of the embodiments disclosed herein, the apparatus may further comprise an articulable bracket positioned between the second jaw and the body, wherein the second jaw may be slidingly coupled to the articulable bracket such that the second jaw is independently movable with respect to the articulable bracket as the articulable bracket is movable with respect to the body In accordance with any of the embodiments disclosed herein, the articulable bracket may cause the second jaw to travel along an arcuate path toward the first jaw.

In accordance with any of the embodiments disclosed herein, the second jaw may be slidable with respect to the articulable bracket along a linear path disposed at an angle from the lateral portion of the mounting structure such that as the motor actuates the second jaw toward the second position, the fourth surface of the second jaw moves toward the lateral portion of the mounting structure In accordance with any of the embodiments disclosed herein, the first jaw may be slidable with respect to the body along a linear path disposed at an angle from the lateral portion of the mounting structure such that as the motor actuates the second jaw toward the second position, the second surface of the first jaw moves toward the lateral portion of the mounting structure.

DESCRIPTION OF THE DRAWINGS

Many aspects of the present disclosure can be better understood with reference to the detailed description along with the following drawings. The components in the drawings are not necessarily drawn to scale. Instead, emphasis is placed on illustrating clearly the principles of the present disclosure. Furthermore, components can be shown as transparent in certain views for clarity of illustration only and not to indicate that the component is necessarily transparent. Components may also be shown schematically.

FIGS. 2A and 2B are front-right-top and rear-right-top perspective views, respectively, of a modular clamp assembly configured in accordance with embodiments of the present disclosure.

FIGS. 3A and 3B are front-right-top and rear-right-top perspective views, respectively, of a modular clamp assembly configured in accordance with embodiments of the present disclosure.

In the specification, it should be appreciated that like reference numerals are used to identify like elements illustrated in one or more of the figures for purposes of illustrating embodiments of the present disclosure and not for purposes of limiting the same.

DETAILED DESCRIPTION

Figure 1A:
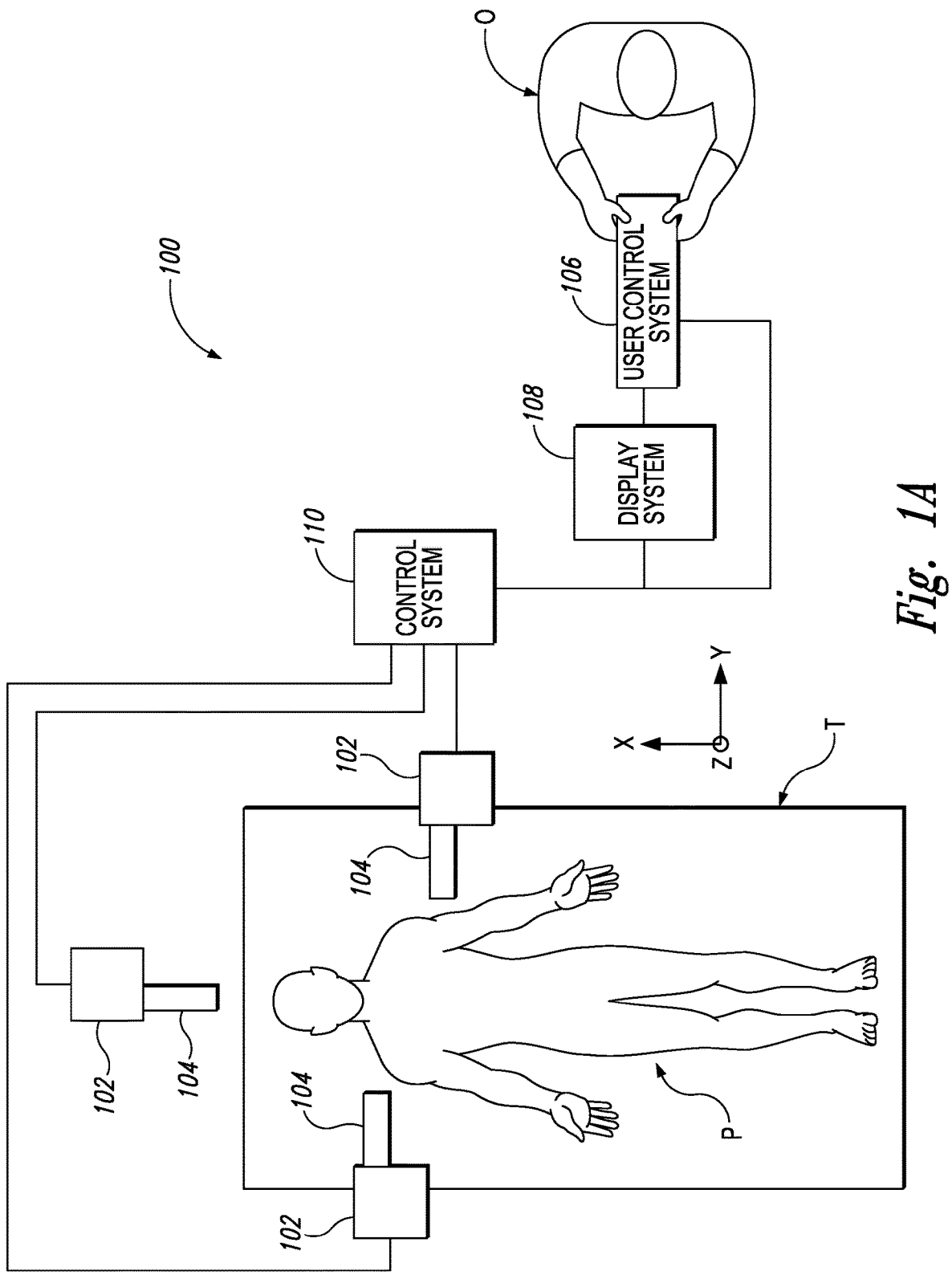
FIG. 1A is a simplified diagram of a medical system configured in accordance with an embodiment of the present disclosure.

The present disclosure generally relates to a modular clamp for mounting a tool (e.g., a surgical arm) to a structure. The modular clamps disclosed herein may have adapter features that are configured to allow mounting of various tools to the modular clamp, either rigidly or with one or more degrees of freedom (DOF). The modular clamps may be configured to accommodate different mounting structures, e.g., rectangular mounting rails having a range of heights, widths, and/or depths. In addition, modular clamps configured in accordance with the present disclosure may be adapted to accommodate further shapes and sizes of mounting structures, such as rails having different sizes. For example, the clamps may be used to accommodate different rails with different rail sizes. As another example, the clamps may be used to accommodate different portions of a single rail where the different portions have different rail sizes. The clamps may also allow repositioning of one or more components attached to the clamp without removal of the component from the clamp, such as by one or more accessory mounting locations, among other features. Such mounting locations may have coupling features, such as detents or other retention features, to retain the other components in the mounting location until removal from the clamp is desired, e.g., manual rotation of the component to release, overcoming the detent, etc. Mounting location(s) may be illuminated to aid in coupling the component to the clamp. The clamps may include various openings, slots, and indices for one or more auxiliary features, such as cable routing, connector mounting, positioning of the clamp, etc. In some embodiments with cable routing, the mounting location may include a connector to connect a signal cable routed through the clamp to a signal cable of the mounted component upon coupling. The clamps having electrical clamping features may also include a manual release lever that can be pivoted to release the clamp from the mounting structure.

Certain mounting systems described throughout this disclosure are appropriately configured to retrofit a conventional operating table in a manner that provides a robust and stable mounting point for securing a teleoperated surgical arm to the table. Continued development of teleoperated surgical systems has led to the implementation of individual surgical arms that can be received and supported by a relatively compact interface. The interface can be a part of a portable module positionable near a patient's body and secured to an operating room structure (e.g., an operating table) by medical staff prior to a surgical procedure. This modular configuration provides an alternative to other arrangements where one or more surgical arms are attached to a comparatively large support assembly on a stand-alone structure. Accordingly, one advantage that may be gained from implementing such a modular system is more efficient space utilization in an operating room.

Various embodiments described within this disclosure are derived from a realization that many existing operating tables were not designed to support a teleoperated surgical arm. Nevertheless, it may be desirable and advantageous to use the operating table's side rails for mounting a teleoperated robotic surgical arm and/or other associated tools for multiple reasons. First, the rails are conveniently located on a side of the operating table, and therefore proximate the target location of the surgical arm, i.e., near the patient. Second, the side rails allow a variety of objects to be readily attached to the operating table by clamps (or other similar coupling devices).

Accordingly, the present disclosure describes various mounting systems that can be attached to an operating table in a manner that adds stability to the standard side rails, offering a robust and sturdy mounting point to secure a surgical arm or associated tool during a surgical procedure. Employing the mounting systems described herein enables the use of surgical arms with pre-existing operating tables, which allows a medical facility to obtain the benefits of teleoperated minimally invasive surgery at lower cost.

Embodiments of the modular clamp assemblies described below include various clamping and releasing arrangements with jaws having various degrees of freedom. In this regard, the embodiments can include automated electro-mechanical actuation, manual electro-mechanical actuation, and/or manual mechanical actuation. Although some of the embodiments are shown with or without electro-mechanical components, any of the embodiments described herein are adaptable for either electro-mechanical or mechanical actuation. Generally described, the modular clamp assemblies described below have the following configurations: (A) the arrangement shown in FIGS. 2A-2G is electro-mechanical having an upper jaw with one degree of freedom and a lower jaw with two degrees of freedom; (B) the arrangement shown in FIGS. 3A-3F is electro-mechanical having a lower jaw with one degree of freedom; (C) the arrangement shown in FIGS. 4A-4H is mechanical having a lower jaw with two degrees of freedom; and (D) the arrangement shown in FIGS. 5A-5H is mechanical having a lower jaw with one degree of freedom. In other embodiments of the present disclosure, each of the arrangements disclosed herein may be adapted such that the upper jaw and/or lower jaw have any number of degrees of freedom.

The present disclosure describes various instruments and portions of instruments in terms of their state in three-dimensional space. As used herein, the term position refers to the location of an object or a portion of an object in a three-dimensional space (e.g., three degrees of translational freedom along Cartesian X-, Y-, and Z-coordinates). As used herein, the term orientation refers to the rotational placement of an object or a portion of an object (e.g., three degrees of rotational freedom, such as roll, pitch, and yaw). As used herein, the term pose refers to the position of an object or a portion of an object in at least one degree of translational freedom and to the orientation of that object or portion of the object in at least one degree of rotational freedom (e.g., up to six total degrees of freedom). As used herein, the term shape refers to a set of poses, positions, or orientations measured along an object.

FIG. 1A is a simplified diagram of a medical system 100 ("system 100"). In some embodiments, the system 100 may be suitable for use in, for example, surgical, teleoperated surgical, diagnostic, therapeutic, or biopsy procedures. While some embodiments are provided herein with respect to such procedures, any reference to medical or surgical instruments and medical or surgical methods is intended as non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the clamps, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

As shown in FIG. 1A, the system 100 generally includes a plurality of manipulator assemblies 102. Although three manipulator assemblies 102 are illustrated in the embodiment of FIG. 1A, in other embodiments, more or fewer manipulator assemblies may be used. The exact number of manipulator assemblies will depend on the medical procedure and the space constraints within the operating room, among other factors. Multiple user control systems 106 may be co-located or they may be positioned in separate locations. Multiple user control systems 106 allow more than one operator to control one or more teleoperated manipulator assemblies in various combinations.

The manipulator assembly 102 is used to operate a medical instrument 104 (e.g., a surgical instrument or an image capturing device) in performing various procedures on a patient P. The medical instrument 104 may be sterile prior to being used in the various procedures. The manipulator assembly 102 may be teleoperated, non-teleoperated, or a hybrid teleoperated and non-teleoperated assembly with select degrees of freedom of motion that may be motorized and/or teleoperated, and select degrees of freedom of motion that may be non-motorized and/or non-teleoperated. In some embodiments, the manipulator assembly 102 may be mounted near an operating or surgical table T, or the manipulator assembly 102 may be mounted directly to the table T or to a rail coupled to the table T. In various other embodiments, the manipulator assembly 102 may be mounted to a manipulating system (e.g., a patient-side cart). The manipulating system may be separate from and spaced from the table T in the operating room and may be independently movable relative to the table T.

The manipulator assembly 102 may be mounted to a ceiling, floor, and/or wall of the operating room. In embodiments in which a plurality of manipulator assemblies 102 are employed, one or more of the manipulator assemblies 102 may support surgical instruments, and another of the manipulator assemblies may support an image capturing device such as a monoscopic or stereoscopic endoscope. In such embodiments, one or more of the manipulator assemblies 102 may be mounted to any structure or in any manner as described above. For example, one manipulator assembly 102 may be mounted to the table T and another manipulator assembly 102 may be mounted to a manipulating system.

A user control system 106 allows an operator (e.g., a surgeon or other clinician, as illustrated in FIG. 1A) to view the interventional site and to control the manipulator assembly 102. In some examples, the user control system 106 is a surgeon console, which can be located in the same room as the operating or surgical table T, such as at the side of a table on which the patient P is located. However, the operator O can be located in a different room or a completely different building from patient P. The user control system 106 generally includes one or more input devices for controlling the manipulator assembly 102. The input devices may include any number of a variety of devices, such as joysticks, trackballs, data gloves, trigger-guns, hand-operated controllers, voice recognition devices, body motion or presence sensors, and/or the like. The input devices may be provided with the same degrees of freedom as the associated medical instrument 104 to provide the operator O a strong sense of directly controlling the medical instrument 104. In this regard, the input devices may provide the operator O with telepresence: the perception that the input devices are integral with medical instrument 104.

The input devices may have more or fewer degrees of freedom than the associated medical instrument 104 and still provide the operator O with telepresence. The input devices may optionally be manual input devices that move with six degrees of freedom, and may also include an actuatable handle for actuating instruments (for example, for closing grasping jaws, applying an electrical potential to an electrode, delivering a medicinal treatment, etc.).

The manipulator assembly 102 may support the medical instrument 104 and may include a kinematic structure of one or more non-servo controlled links (e.g., one or more links that are manually positioned and locked in place), and/or one or more servo controlled links (e.g., one or more links that are controlled in response to commands from a control system), and a manipulator. The manipulator assembly 102 may optionally include a plurality of actuators or motors (described in greater detail below) that drive inputs on the medical instrument 104 in response to commands from the control system (e.g., a control system 110). The actuators may optionally include drive systems that when coupled to the medical instrument 104 may advance the medical instrument 104 into a naturally or surgically created anatomic orifice.

Other drive systems may move the distal end of the medical instrument 104 in multiple degrees of freedom, which can include three degrees of linear motion (e.g., linear motion along the X, Y, Z Cartesian axes), and three degrees of rotational motion (e.g., rotation about the X, Y, Z Cartesian axes). Additionally, the actuators can be used to actuate an articulable end effector of the medical instrument 104, e.g., for grasping tissue in the jaws of a biopsy device. Actuator position sensors such as resolvers, encoders, potentiometers, and other mechanisms may provide sensor data to the system 100 describing the rotation and orientation of the shafts of the actuator. Such position sensor data may be used to determine motion of the objects manipulated by the actuators. The manipulator assembly 102 may position its held instrument such that a pivot point occurs at the entry aperture into the patient. The manipulator assembly 102 may then manipulate its held instrument so that the instrument may be pivoted about the pivot point, inserted into and retracted out of the entry aperture, and/or rotated about its shaft axis.

The system 100 may also include a display system 108 for displaying an image or representation of the surgical site and the medical instrument 104. The display system 108 and the user control system 106 may be oriented so the operator O can control the medical instrument 104 and the user control system 106 with the perception of telepresence. The medical instrument 104 may include a visualization system, which may include a viewing scope assembly that records a concurrent or real-time image of a surgical site and provides the image to the operator O and/or other operators or personnel through one or more displays of the system 100, such as one or more displays of the display system 108. The concurrent image may be, for example, a two- or three-dimensional image captured by an endoscope positioned within the surgical site. The visualization system may be implemented as hardware, firmware, software, or a combination thereof that interact with or are otherwise executed by one or more computer processors that may include the processors of the control system 110. The display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images, and/or as images from models created from the pre-operative or intra-operative image data sets.

The system 100 may also include the control system 110. The control system 110 may include at least one memory (not shown) and at least one computer processor (not shown) for effecting control between the medical instrument 104, the user control system 106, and the display system 108. The control system 110 also includes programmed instructions (e.g., a non-transitory machine-readable medium storing the instructions) to implement some or all the methods described in accordance with aspects of the present disclosure disclosed herein, including instructions for providing information to the display system 108. While the control system 110 is shown as a single block in the simplified schematic of FIG. 1A, the system may include two or more data processing circuits with one portion of the processing optionally being performed on or adjacent to the manipulator assembly 102, another portion of the processing being performed at the user control system 106, etc. The processors of the control system 110 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, the control system 110 supports wireless communication protocols such as Bluetooth, IrDA, HomeRF, IEEE 802.11, DECT, and Wireless Telemetry.

In some embodiments, a communication is sent from the control system 110 to the manipulator assembly 102. Additionally, status information regarding testing of the manipulator assembly 102 may be sent from a sterile storage container (not shown) to the control system 110. This status information is used to optimize the performance of the system 100 by indicating an operational status of one or more components of the manipulator assembly 102. The status information may additionally be received by the operator O, a surgeon, and/or any other suitable personnel. The status information may also be received by a hospital information system, a patient information portal, a surgical information database, and/or any other suitable information system or database. In some embodiments, the status information is sent to a manufacturer of the manipulator assembly 102 to indicate whether the manipulator assembly 102 or any other component of the system requires maintenance.

Movement of the manipulator assembly 102 may be controlled by the control system 110 such that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, the risk of excessive lateral motion of the shaft that might potentially cause hazardous forces on the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions, or may in part or in full be imposed using data processing and control techniques. In some embodiments, the control system 110 may receive force and/or torque feedback from the medical instrument 104. Responsive to the feedback, the control system 110 may transmit signals to the user control system 106. In some examples, the control system 110 may transmit signals instructing one or more actuators of the manipulator assembly 102 to move the medical instrument 104.

Figure 1B:
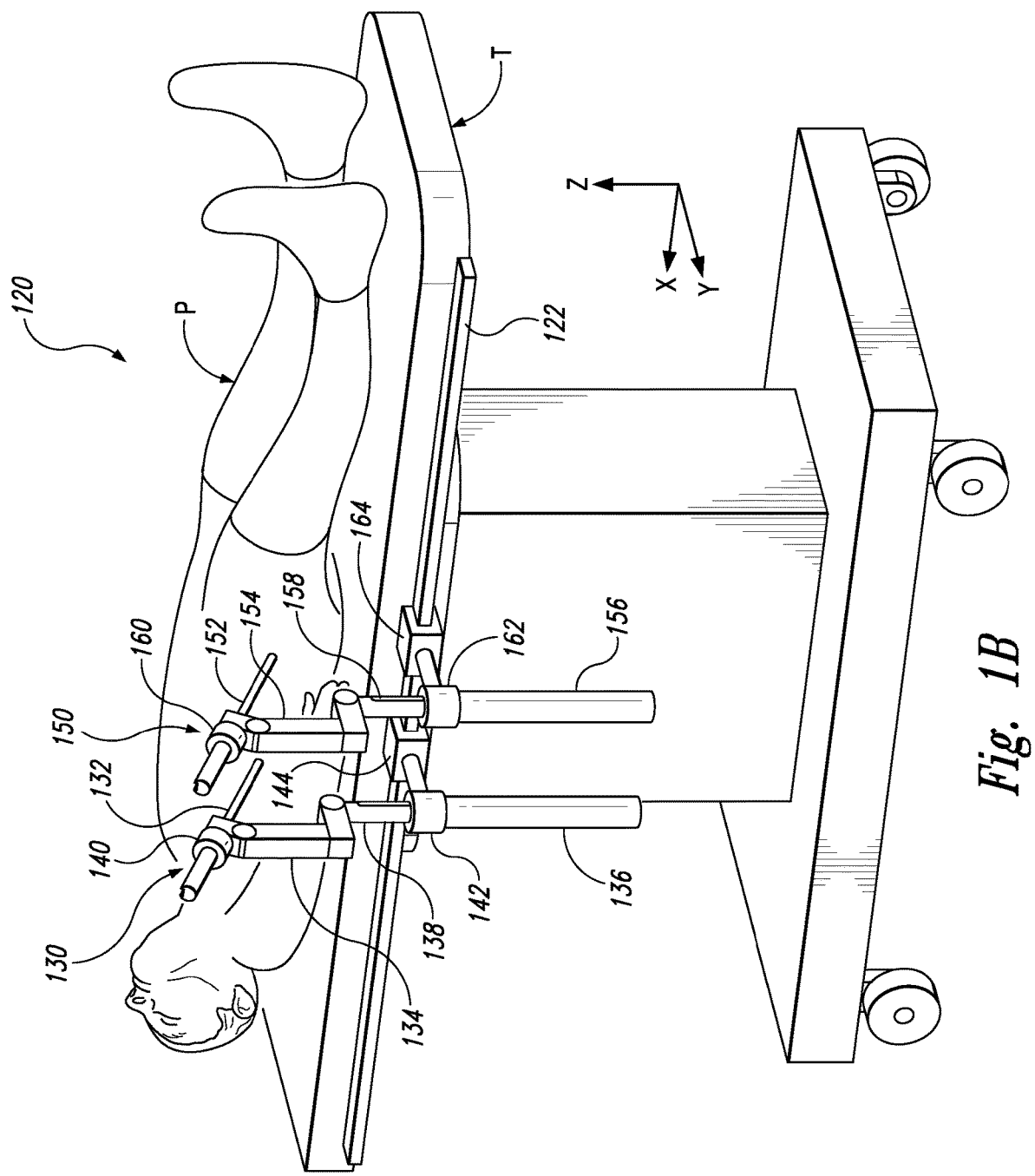
FIG. 1B is a perspective view of a structural representation of the medical system of FIG. 1A.

FIG. 1B is a perspective view of a patient coordinate space 120 including first and second teleoperated surgical manipulator assemblies 130 and 150 mounted on a side of a surgical table T according to one or more aspects of the present disclosure. The first and second manipulator assemblies 130 and 150 may be used as the manipulator assembly 102 (FIG. 1A) in a medical procedure performed with the system 100 and controlled by the control system 110. The first and second manipulator assemblies 130 and 150 may be used in procedures involving traditional manually operated minimally invasive surgical instruments, such as manual laparoscopy. While only the first and second manipulator assemblies 130 and 150 are depicted, more than two (e.g., three, four, five, six, and more than six) or fewer than two manipulator assemblies can be included in some configurations of the system 100.

Figure 3C:
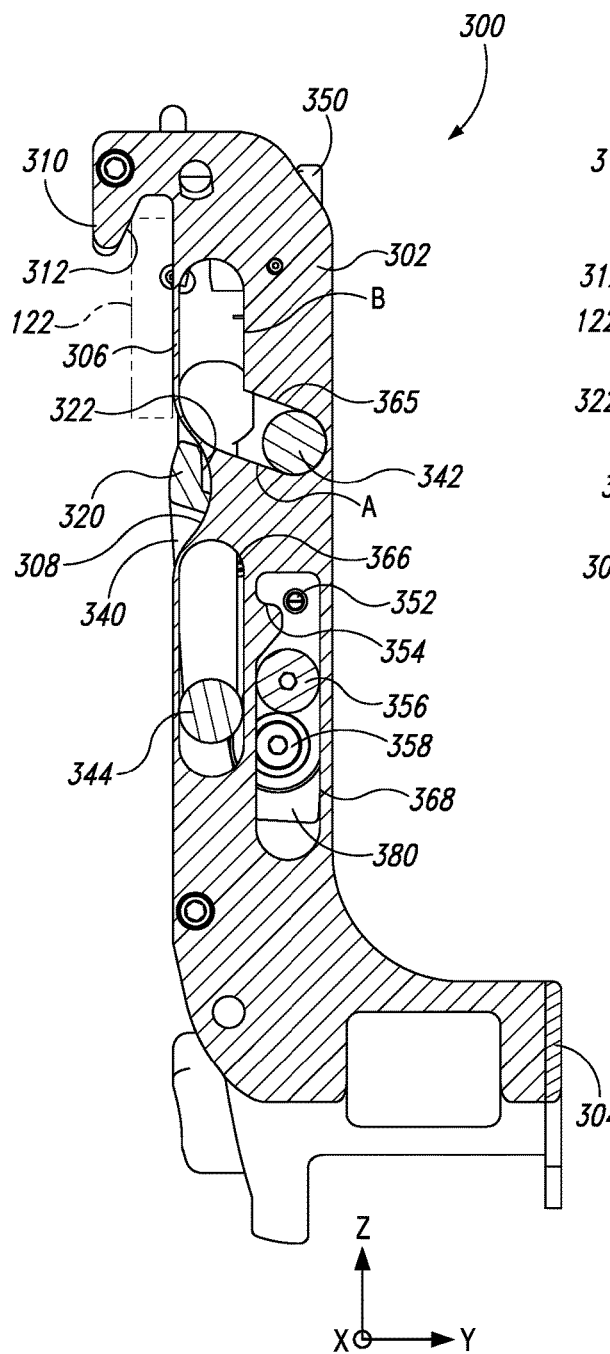
FIGS. 3C-3F are cross-sectional right side views of the modular clamp assembly of FIGS. 3A and 3B, with the cross-sections taken along corresponding positions shown in FIGS. 3A and 3B.
Figure 3D:
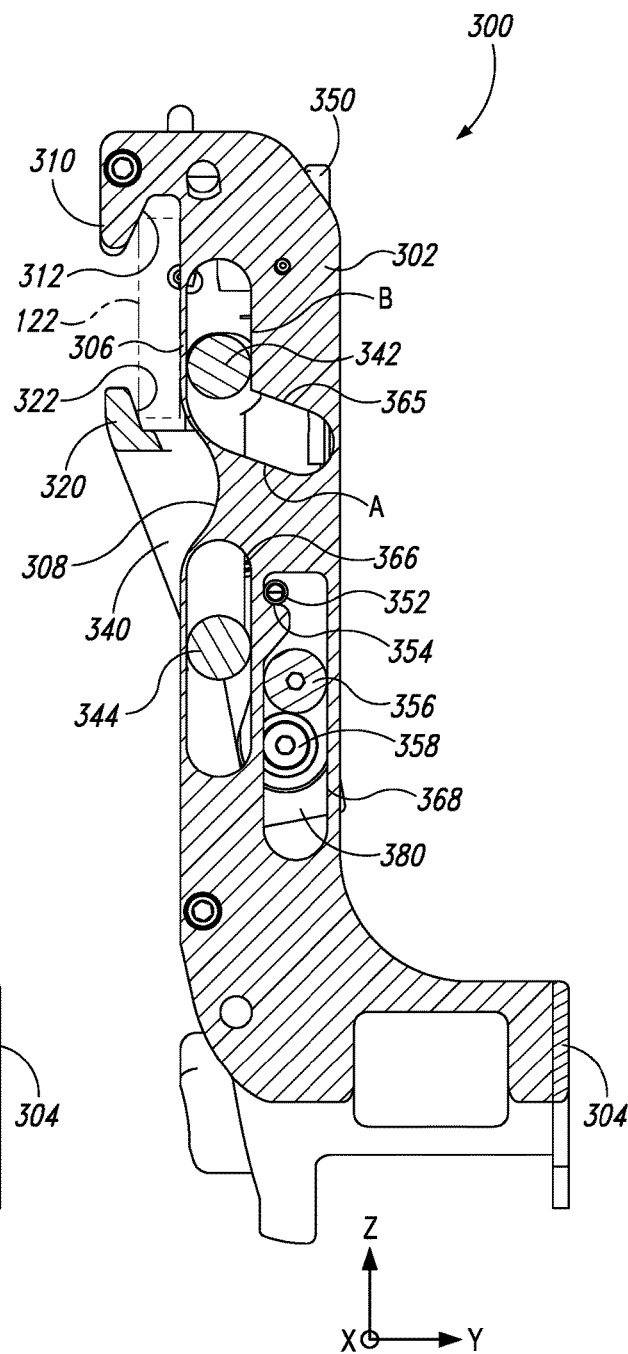

A mounting structure 122 (e.g., an equipment rail, an equipment channel, etc.) may be configured such that the first and second manipulator assemblies 130 and 150 can be mounted to the table T during the medical procedure. The mounting structure 122 may differ in size and/or shape (e.g., height, width, etc.) between manufacturers, models, vintages, etc. In some embodiments, the mounting structure 122 of a single table T may have portions with different sizes and/or shapes. For example, the mounting structure 122 may have a first portion with a first size and/or shape and a second portion with a second size and/or shape different than the first portion, as well as additional other portions with different sizes and/or shapes. As described in more detail below, components mounting to the mounting structure 122, such as the embodiments described herein, can be configured to accommodate different sizes and shapes of the mounting structure 122 without changing configurations and/or manual adjustment. As referenced herein, the mounting structure 122 may generally have an aspect ratio where the height of the mounting structure is greater than the width of the mounting structure, e.g., a rail with a rectangular profile as shown in FIGS. 3C, 3D, etc. In this regard, the mounting structures described herein may be rotated 90° from the orientation of the mounting structure shown in FIG. 1B.

In some embodiments, the mounting structure 122 may be attached to a manipulating system (e.g., a patient-side cart, a side table, etc.). The first manipulator assembly 130 may operably move a first instrument 132 within the patient coordinate space 120, and the second manipulator assembly 150 may operably move a second instrument 152 within the patient coordinate space 120. The first and second instruments 132 and 152 can be sterilized prior to use in a medical procedure. In this regard, the sterile boundary may be positioned above, below, or intermediate to the clamps described in the embodiments of the present disclosure. One or more drapes (not shown) may be used to maintain a sterile field, and the edges of the clamps described herein may be configured to reduce sharp edges that could abrade or otherwise tear the drapes. Various mounting arrangements and configurations manipulator assemblies are described in U.S. application Ser. No. 16/408,077 (filed May 9, 2019, titled "Mounting Teleoperated Surgical Arms"), which is incorporated by reference herein in its entirety.

The first manipulator assembly 130 may include a first manipulator 134, a first link 138, and a first drive unit 140. The second manipulator assembly 150 may include a second manipulator 154, a second link 158, and a second drive unit 160. The first instrument 132 may be coupled to the first drive unit 140, and the second instrument 152 may be coupled to the second drive unit 160. In some embodiments, the first drive unit 140 is, for example, a standalone unit including a system of drive mechanisms (not shown, e.g., motors). The first drive unit 140 may be operated to control motion of the first instrument 132 in multiple DOFs when the first instrument 132 is mounted to the first drive unit 140. The second drive unit 160 may be similarly configured for operation of the second instrument 152. The first drive unit 140 may be coupled to the first manipulator 134, and the second drive unit 160 may be coupled to the second manipulator 154. The first manipulator 134 may be movably coupled to the first link 138, and the second manipulator 154 may be movably coupled to the second link 158.

Any one or more of the components of the first manipulator 134, the second manipulator 154, the first drive unit 140, and/or the second drive unit 160 may be teleoperated. Further, many of the components (the first and second instruments 132 and 152; the first and second drive units 140 and 160; the first and second manipulators 134 and 154; and the first and second links 138 and 158) may be sterilized prior to use in a medical procedure. Additionally, one or more of the input devices (e.g., joysticks, trackballs, data gloves, trigger-guns, hand-operated controllers, voice recognition devices, body motion or presence sensors, and/or the like), which may be used for controlling the manipulator assembly 102 (FIG. 1A), may be sterilized prior to use in a medical procedure.

In embodiments where the first manipulator assembly 130 is mounted to the mounting structure 122 of the surgical table T, the manipulator assembly 130 may be coupled with a first coupling member 142 and a first clamp 144 to the surgical table T. The first coupling member 142 may be a joint (e.g., a ball joint, a spherical ball joint, a prismatic joint, a gimbal, etc.). The second manipulator assembly 150 may be coupled to the surgical table T by a second coupling member 162 and a second clamp 164. A first housing 136 may be coupled to the first coupling member 142, and a second housing 156 may be coupled to the second coupling member 162. In some embodiments, the first manipulator assembly 130 includes the first coupling member 142, the first clamp 144, and the first housing 136, and the second manipulator assembly 150 includes the second coupling member 162, the second clamp 164, and the second housing 156.

The first manipulator assembly 130 may be coupled to the mounting structure 122 of the surgical table T by the first clamp 144. The first clamp 144 (which may be a support component and/or a support structure) may kinematically support the first manipulator 134 and, therefore, the first manipulator assembly 130 before, during, and/or after a surgical procedure. The first clamp 144 may translate along the mounting structure 122 to allow the position of the first manipulator assembly 130 to be moved or readjusted relative to the table T and the patient P. The first clamp 144 may be coupled to the table T via the mounting structure 122, or may be coupled directly to the table T. In other embodiments, the first clamp 144 can be coupled directly to the first housing 136 or the first link 138 without the first coupling member 142. In some embodiments, the first clamp 144 can be coupled to a separate cart that is positioned near or attached to the table T.

The second manipulator assembly 150 may be coupled to the mounting structure 122 of the surgical table T by the second clamp 164. The second clamp 164 (which may be a support component and/or a support structure) may kinematically support the second manipulator 154 and, therefore, the second manipulator assembly 150 before, during, and/or after a surgical procedure. The second clamp 164 may translate along the mounting structure 122 to allow the position of the second manipulator assembly 150 to be moved or readjusted relative to the table T and the patient P. The second clamp 164 may be coupled to the table T via the mounting structure 122, or may be coupled directly to the table T. In other embodiments, the second clamp 164 can be coupled directly to the second housing 156 or the second link 158 without the second coupling member 162. In some embodiments, the second clamp 164 can be coupled to a separate cart that is positioned near or attached to the table T.

Movement of the first and second manipulator assemblies 130 and 150 (e.g., insertion, rotation, translation, etc.) can be actuated by either robotic control or by manual intervention by the operator O. For example, the position and orientation of the first and second manipulator assemblies 130 and 150 may be maintained in a stationary configuration using one or more brakes. However, depression of one or more buttons and/or switches may release one or more corresponding brakes, allowing the operator O to manually reposition either of the first and second manipulator assemblies 130 and 150, to thereby position the medical instrument 104. One or more adjustments may also be controlled by one or more actuators (e.g., motors) such that the operator O may use a button or switch to actuate a motor to alter either of the first and second manipulator assemblies 130 and 150 in a desired manner to position either of the first and second manipulator assemblies 130 and 150 in the optimal position and orientation.

FIGS. 2A and 2B are front-right-top and rear-right-top perspective views, respectively, of a modular clamp assembly ("clamp 200") configured in accordance with embodiments of the present disclosure. The clamp 200 is configured to be removably attached to a mounting structure such that various components and tools can be mounted to or supported by the clamp 200 and modularly arranged with respect to the mounting structure. In some embodiments, the mounting structure is a rail of the table T shown in FIGS. 1A and 1B, and the clamp 200 is configured to support one or more of the components described above in reference to the first and second manipulator assemblies 130 and 150 (FIG. 1B). In this regard (and with reference to FIG. 1B) the clamp 200 may be operatively associated with the instruments 132 and 152, the manipulators 134 and 154, the housings 136 and 156, the links 138 and 158, the drive units 140 and 160, the coupling members 142 and 162 in the system 100, and may replace the illustrated clamps 144 and 164 of FIG. 1B. In other embodiments, any rigid, adjustable, and/or positionable system may be mounted to the table T or other manipulating system (e.g., a patient-side cart) using the clamp 200. As shown, such clamps 200 may allow adaptation of the configuration of one or more manipulator assemblies tailored to the anatomy of the patient P, the procedure to be performed, the preference of the operator O, the layout of the patient coordinate space 120, etc.

The clamp 200 generally includes a body 202 configured to at least partially surround and protect various components of the clamp 200, provide component positioning and dynamic features, and include one or more accessory mounting locations, among other features. The body 202 may include a distal mounting location 204 configured to couple to other components of the system 100, e.g. the coupling members 142 and 162. In other embodiments, the body 202 includes any number of mounting locations to adapt the clamp 200 for mounting various other components. Examples of various components that may be coupled to the distal mounting location 202 or other mounting locations on the body 202 are described in U.S. Pub. No. 2019/0223967 (filed Oct. 4, 2017, titled "Computer-Assisted Teleoperated Surgery Systems and Methods") and which is incorporated by reference herein in its entirety. In any of the embodiments of the present disclosure, the mounting locations have coupling features, such as detents or other retention features, to retain mounted components in the mounting location until removal is desired, e.g., manual rotation of the component to release, overcoming the detent, etc. The clamps described herein may also be removed from the mounting structure (e.g., the mounting structure 122) without removing the component coupled to the clamp, and the mounting location may be illuminated to aid in coupling the component to the clamp. The body 202 may include other features, such as various openings, slots, and indices (not shown with respect to the clamp 200, but explained in greater detail below in reference to other embodiments of the present disclosure) for one or more auxiliary features of the clamp 200, such as cable routing, connector mounting, positioning of the clamp, etc. In some embodiments with cable routing, the mounting location may include a connector to connect a signal cable routed through the clamp to a signal cable of the mounted component upon coupling. The clamp 200 may also include a manual release lever 250 (FIG. 2B) that can be pivoted in the direction of arrow O to release the clamp 200 from the mounting structure. The manual release lever 250 will be explained in greater detail with reference to FIGS. 2C and 2D below.

The clamp 200 may include a movable upper jaw 210 and movable lower jaw 220 configured to interface with a variety of mounting structures (e.g. the mounting structure 122) to couple the clamp 200 to the mounting structure such that, for example, components of the first and second manipulator assemblies 130 and 150 can be arranged and articulated with respect to the mounting structure. The upper jaw 210 may include an upper projection 212 to partially enclose a section of the mounting structure 122 in a lateral direction (e.g., the Y-direction) when the clamp 200 has a clamped mechanical state (is "clamped") on the mounting structure 122, as will be explained in greater detail below. As illustrated, the clamp 200 may include a pair of upper jaws 210 in a spaced apart configuration having an upper spacer 218 therebetween. In other embodiments, the clamp 200 has a continuous jaw portion and upper projection extending across the entire width of the upper jaw, or has any number of jaw segments and/or projections across the width of the upper jaw.

The upper jaw 210 may be movable with respect to an upper jaw housing 230 of the body 202. In this regard, the upper jaw 210 may be slidingly adjustable in at least one DOF with the upper jaw housing 230 by receiving an upper stem 232 coupled to the upper jaw 210. As illustrated, a pair of upper stems 232 may be inserted through openings in the upper jaw housing 230 corresponding to each of the pair of upper jaws 210. However, in other embodiments, any number of upper stems can be used to allow constrained movement of the upper jaws 210 with respect to the body 202. The interface of the upper jaw 210 and upper stem 232 with the upper jaw housing 230 may include a biasing member 234 (e.g., a spring) configured to bias the upper jaw 210 and upper stem 232, for example, away from the upper jaw housing 230. The interface of the upper stem 232 and the upper jaw housing 230 may include a stop (e.g., a retaining clip, bushing, plug, etc. not shown) to prevent detachment of the upper stem 232 from the upper jaw housing 230 (e.g., as a result of the force of the biasing member 234 and/or other forces such as gravity). As will be explained in greater detail below, the biasing member 234 may be compressed as the upper jaw 210 translates with respect to the upper jaw housing 230 during attachment of the clamp 200 to a mounting structure.

The movable lower jaw 220 may include a lower projection 222 to partially enclose the mounting structure 122 in a lateral direction when the clamp 200 is clamped on the mounting structure 122. As illustrated, the clamp 200 may include a pair of lower jaws 220 in a spaced apart configuration having a lower spacer 228 therebetween. As with the upper jaw 210, in other embodiments, the clamp 200 has a continuous jaw portion and lower projection extending across the entire width of the lower jaw, or has any number of jaw segments and/or projections across the width of the lower jaw. In some embodiments, the lower jaws 220 may be offset from the upper jaws 210 (e.g., in the X-direction).

The lower jaw 220 may be movable with respect to the body 202 by an articulable bracket 240 adjustable in at least one DOF with the body 202. The lower jaw 220 may also be slidingly adjustable in at least one DOF with the articulable bracket 240 by receiving a lower stem 242 (see FIGS. 2C and 2D) coupled to the lower jaw 220. As illustrated, a pair of lower stems 242 may be inserted through openings in the articulable bracket 240 corresponding to each of the pair of lower jaws 220. However, in other embodiments any number of lower stems can be used to allow constrained movement of the lower jaws 220 with respect to the articulable bracket 240. The interface of the lower jaw 220 and lower stem 242 with the articulable bracket 240 may include a biasing member 244 (e.g., a spring) configured to bias the lower jaw 220 and lower stem 242, for example, away from the articulable bracket 240. The interface of the lower stem 242 and the articulable bracket 240 may include a stop (e.g., a retaining clip, bushing, plug, etc. not shown) to prevent detachment of the lower stem 242 from the articulable bracket 240 (e.g., as a result of the force of the biasing member 244 or other forces). As will be explained in greater detail below, the biasing member 244 may be compressed as the lower jaw 220 translates with respect to the articulable bracket 240 during attachment of the clamp 200 to a mounting structure.

Figure 2C:
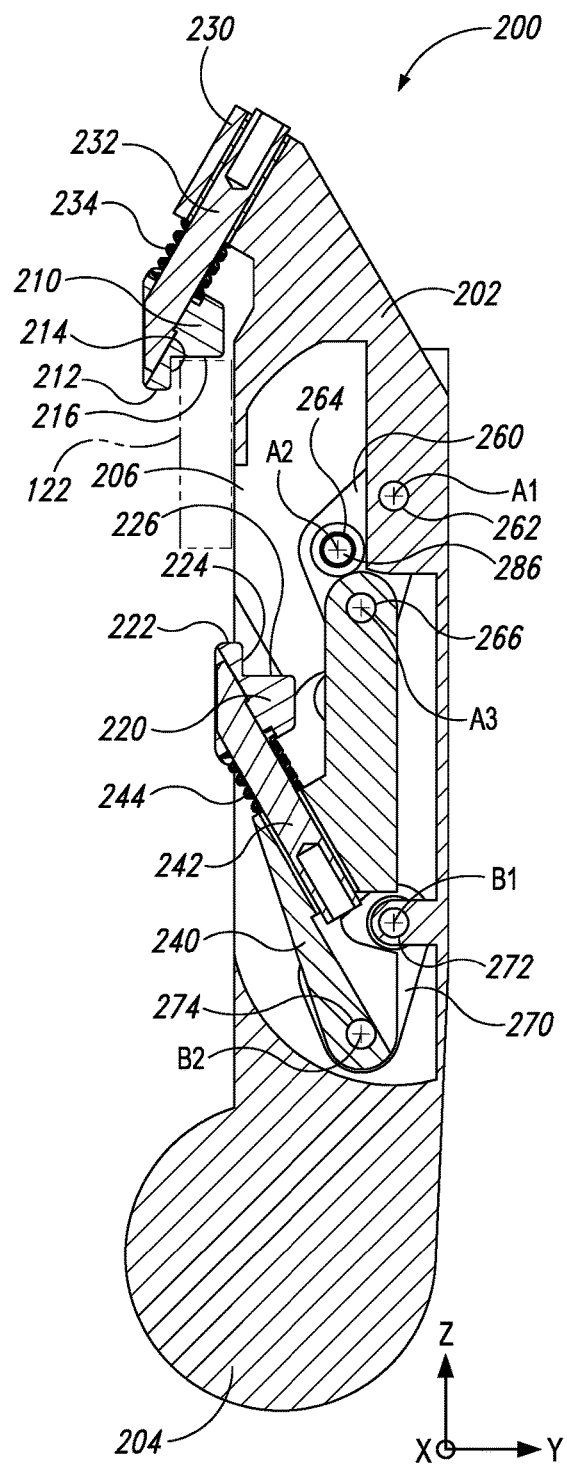
FIGS. 2C-2F are cross-sectional right side views of the modular clamp assembly of FIGS. 2A and 2B, with the cross-sections taken along corresponding positions shown in FIGS. 2A and 2B.

FIGS. 2C-2F show cross-sectional right side views of the clamp 200, the cross-sections taken along corresponding positions shown in FIGS. 2A and 2B. FIG. 2G shows a detail view of certain components of the clamp 200, with the body 202 and the manual release lever 250 hidden for purposes of clarity. In some embodiments, the clamping articulation of the clamp 200 is accomplished by an electric motor 280 (see FIGS. 2E-2G) that moves the articulable bracket 240 to draw the jaws 210 and 220 toward the upper jaw housing 230 and the articulable bracket 240, respectively, and inward toward the body 202 to engage the mounting structure 122 (shown in broken lines).

Figure 2D:
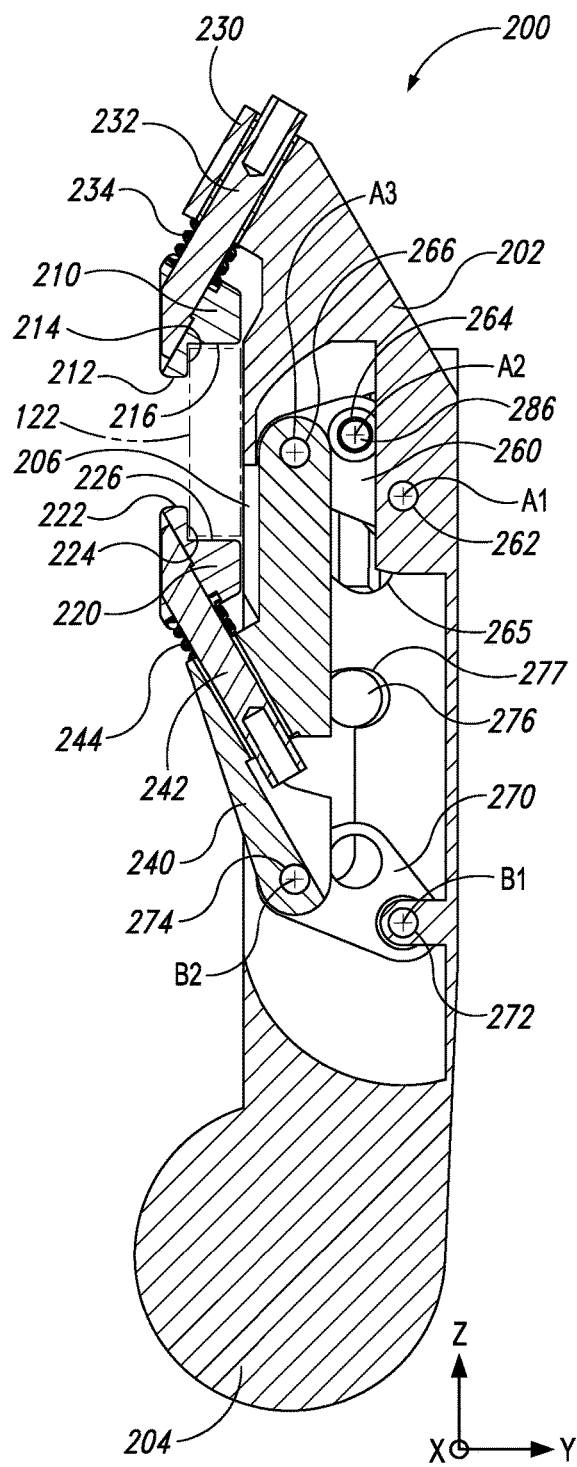

Referring to FIGS. 2C and 2D, the upper jaw 210 includes an upper lateral clamping surface 214 of the upper projection 212 and an upper vertical clamping surface 216. The upper lateral clamping surface 214 and the upper vertical clamping surface 216 may be configured to abut corresponding surfaces of the mounting structure 122 during clamping of the clamp 200. Similarly, the lower jaw 220 includes a lower lateral clamping surface 224 of the lower projection 222 and a lower vertical clamping surface 226. The lower lateral clamping surface 224 and the lower vertical clamping surface 226 may be configured to abut corresponding surfaces of the mounting structure 122 during clamping of the clamp 200. As shown in FIG. 2D, the upper and lower lateral clamping surfaces 214 and 224 may abut the same surface of the mounting structure 122, e.g., a lateral or side surface, and the upper and lower vertical clamping surfaces 216 and 226 may abut opposite surfaces of the mounting structure 122, e.g., the top and bottom surfaces. In this regard, the upper and lower lateral clamping surfaces 214 and 224 may capture the mounting structure 122 against a rail opposing surface 206 of the body 202 such that the mounting structure 122 has opposing pressure on both lateral sides when the clamp 200 is clamped.

Referring to FIGS. 2C-2G together, the articulable bracket 240 may be movable by the electric motor 280 with respect to the body 202. The articulable bracket 240 may be configured to generally follow an arcuate path based on the pivoting movement of an upper cam 260 together with the lower cam 270. As shown in FIGS. 2C and 2D, the upper cam 260 may be pivotably fixed at pivot A1 and the lower cam 270 may be pivotably fixed at pivot B1. In this regard, the upper and lower cams 260 and 270 may freely rotate about pivots A1 and B1, respectively, and such rotation may be facilitated by an upper bearing 262 and a lower bearing 272. In the illustrated embodiments, pivots A1 and B1 are fixed to at least the body 202 such that pivots A1 and B1 do not move with respect to the body 202 during clamping of the clamp 200.

Figure 2E:
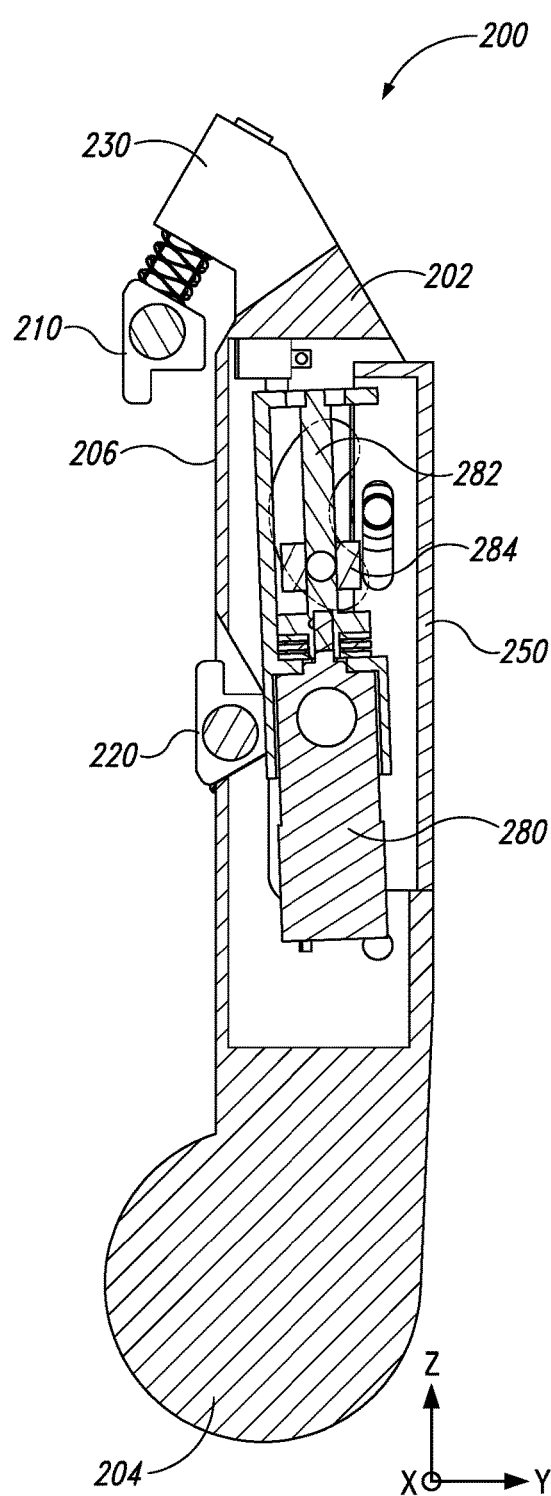
Figure 2F:
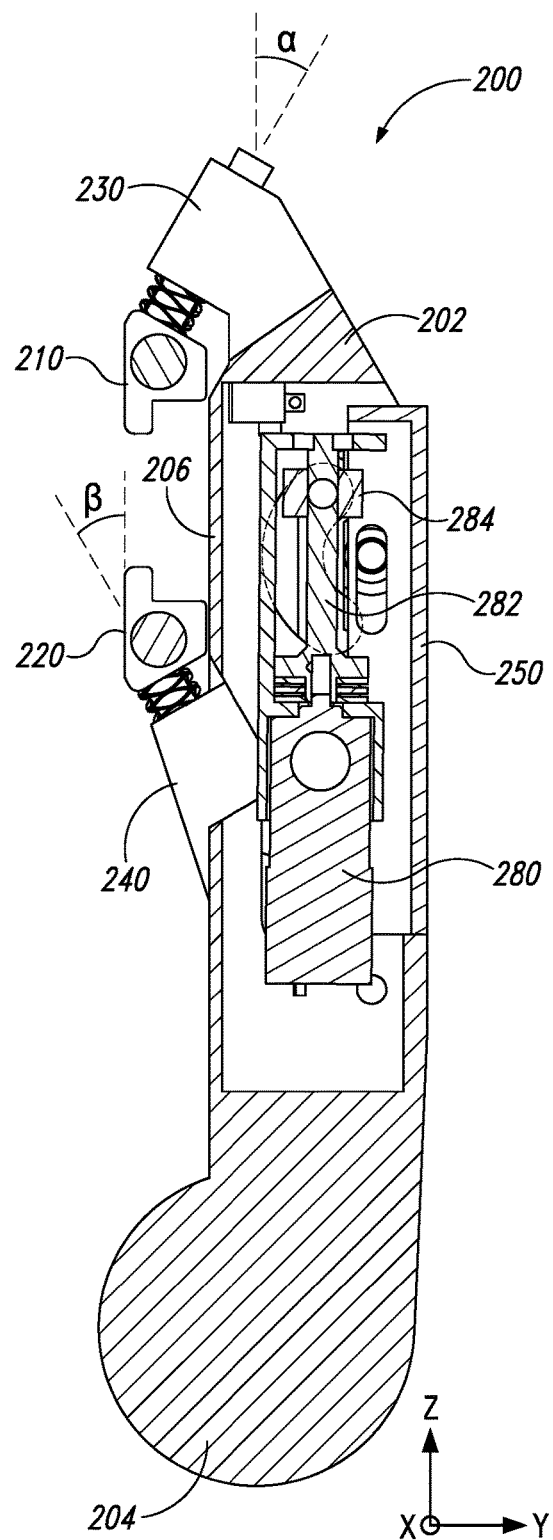
Figure 2G:
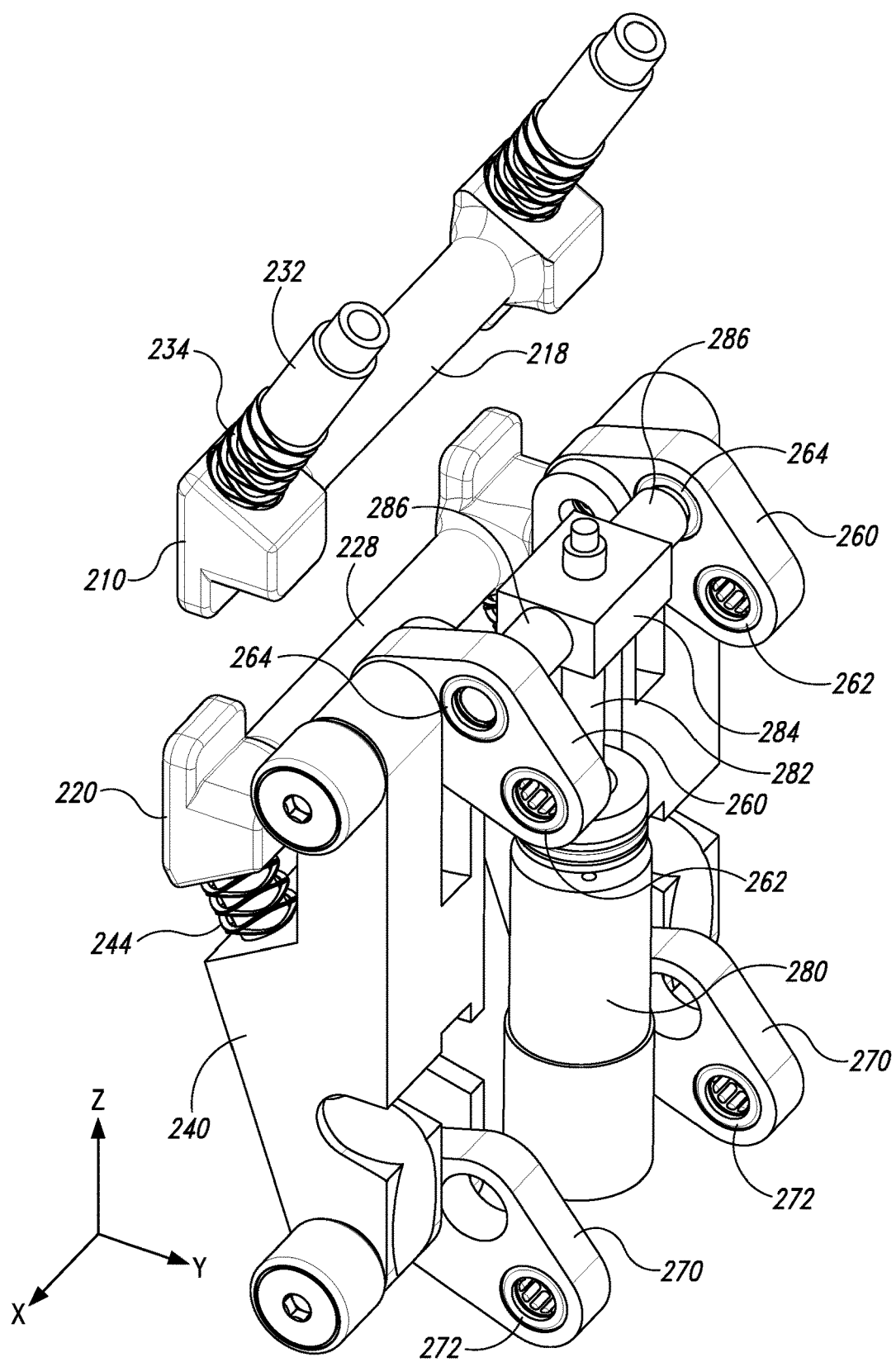
FIG. 2G shows a detail view of certain components of the modular clamp assembly of FIGS. 2A and 2B with the body and the manual release lever hidden for clarity.

The upper cam 260 may include central pivot A2 configured to pivotably interface with a translating rod 286 extending laterally from a junction 284 articulable by the electric motor 280 (see FIGS. 2E-2G). In some embodiments, the junction 284 is movable (e.g., in translation) with respect to the electric motor 280 by a rod 282. The rod 282 may be threaded such that rotation of the electric motor 280 advances or retracts the junction 284 with respect to the electric motor 280, thereby moving the translating rod 286 to effectuate rotation of the upper cam 260. Central pivot A2 may include an upper bearing 264 to facilitate rotation of the upper cam 260 with respect to the translating rod 286 during clamping of the clamp 200. As shown in FIGS. 2C and 2D, the translating rod 286 may travel within an arcuate slot 265 during movement. Although the lower cam 270 is shown having an aperture for a central pivot point, the aperture may be included such that the same cam can be used in both the upper and lower positions to reduce part variation complexity, and the aperture in the lower cam 270 may not be used.

The upper cam 260 may be pivotably fixed to the articulable bracket 240 at pivot A3, and the lower cam 270 may be pivotably fixed to the articulable bracket 240 at pivot B2. In this regard, rotation of the upper and lower cams 260 and 270 about pivots A3 and B2, respectively, may be facilitated by an upper bearing 266 and a lower bearing 274. During movement of the upper and lower cams 260 and 270, e.g., from the position shown in FIG. 2C to that shown in FIG. 2D, the position of the articulable bracket 240 may move while leaving the orientation of the articulable bracket 240 generally static with respect to the body 202. In other embodiments, the upper and lower cams 260 and 270 may have differing lengths, pivots, and/or other geometry such that the orientation of the articulable bracket 240 changes with respect to the body 202 during movement. In these embodiments, certain of the components of the clamp 200, e.g., the upper and lower cams 260 and 270, the arcuate slot 265, etc. may be positioned on either side of the clamp 200 in the X-direction (e.g. in pairs), such that a plurality of these components are used to articulate the clamp 200 during clamping to the mounting structure 122. In other embodiments, components illustrated as having two or more instances, may be used with a single instance, or more instances than illustrated herein, and are within the scope of the present disclosure.

As described above, the manual release lever 250 may be used to override the clamped state (FIG. 2D) of the clamp 200 by pivoting the manual release lever 250 away from the body 202 in the direction of arrow O. As the manual release lever 250 is pivoted away from the body 202, a locking pin 276 releases from a catch 277, allowing the articulable bracket 240 to move from the position in FIG. 2D (clamped) to the position in FIG. 2C (an unclamped mechanical state, or "unclamped").

With reference to FIGS. 2C-2F, movement of the components of the clamp 200 during one representative embodiment of clamping to a mounting structure 122 will now be described in greater detail. The upper jaw 210 and the lower jaw 220 have a translating DOF along axes of the upper stem 232 and the lower stem 242, respectively. The DOF allows the upper and lower jaws 210 and 220 to linearly translate along the upper and lower stems 232 and 242 with respect to the upper jaw housing 230 and the articulable bracket 240, respectively. Initially referring to the unclamped mechanical state shown in FIG. 2C, the upper and lower stems 232 and 242 are fully extended away from the upper jaw housing 230 and the articulable bracket 240, respectively, as a result of the biasing force applied by the biasing members 234 and 244. As the clamp 200 is placed on the rail, one or more sensors (not shown) on the clamp 200 may detect the rail and automatically initiate clamping of the clamp 200. In other embodiments, a user, system, processor, etc. may initiate an automated or manual clamping operation of the clamp 200.

As shown, the upper jaw 210 may be configured to travel along the axis of the upper stem 232 in a direction disposed at an angle $\alpha$ (see FIG. 2F) from vertical (e.g., along the opposing surface 206), and the lower jaw 220 may be configured to travel along the axis of the lower stem 242 in a direction disposed at an angle $\beta$ from vertical. The angles $\alpha$ and $\beta$ may be substantially the same angle from vertical, or the angles $\alpha$ and $\beta$ may differ and be arranged at any suitable angle from vertical. In some embodiments, the angle $\alpha$ is between about 20° and 70° from vertical. In other embodiments, the angle $\alpha$ is between about 25° and 60° from vertical. In further embodiments, the angle $\alpha$ is between about 25° and 45° from vertical. Similarly, in some embodiments, the angle $\beta$ is between about 20° and 70° from vertical. In other embodiments, the angle $\beta$ is between about 25° and 60° from vertical. In further embodiments, the angle $\beta$ is between about 25° and 45° from vertical.

As also shown in FIG. 2C, in the unclamped position, the articulable bracket 240 is positioned downward away from the mounting structure 122 such that the upper and lower cams 260 and 270 are rotated with pivots A3 and B2 in their lowest positions. In this configuration, the opening between the upper and lower jaws 210 and 220 may be maximized to allow ingress of the mounting structure 122 between the upper and lower jaws 210 and 220. As a result of the arcuate path traveled by the pivots A3 and B2 during rotation of the upper and lower cams 260 and 270, respectively, (e.g., along the arcuate slot 265) the articulable bracket 240 may be positioned laterally closer to the body 202 than a position of the articulable bracket 240 at an intermediate point between the unclamped and clamped positions.

Referring to FIGS. 2C-2F, as the electric motor 280 moves the junction 284 upward in the Z-direction, the upper cam 260 rotates about pivot A1 to move the articulable bracket 240 along the arcuate slot 265. For an initial portion of such rotation, the articulable bracket 240 moves upward, causing the lower jaw 220 to approach the mounting structure 122 in the Z-direction, and move laterally outward away from the opposing surface 206 in the negative Y-direction. At a point where a line drawn between pivot A1 and pivot A3 is horizontal, e.g., at the furthest lateral outboard position of the lower jaw 220, further rotation will still cause the articulable bracket 240 to move upward, but will begin moving the lower jaw 220 laterally inward toward the opposing surface 206 via the rotating cams 260 and 270.

When the clamp 200 is initially placed on the mounting structure 122, the upper surface of the mounting structure 122 may contact the upper vertical clamping surface 216 of the upper jaw 210. At a point along the arcuate path of the articulable bracket 240, the lower vertical clamping surface 226 will contact the lower surface of the mounting structure 122, and remain in contact during the remainder of the clamping movement. At this state, the upper and lower stems 232 and 242 will be extended from the upper jaw housing 230 and the articulable bracket 240, respectively, such that the upper and lower lateral clamping surfaces 214 and 222 may be positioned away from the lateral surface of the mounting structure 122 (i.e., not contacting the later surface). As the articulable bracket 240 continues upward along the arcuate path, one or both of the upper and lower jaws 210 and 220 will begin to retract toward the upper jaw housing 230 and the articulable bracket 240, respectively, to cause the jaws 210, 220 to clamp to the mounting structure 122.

In some embodiments, the biasing member 234 will have a force such that the upper jaw 210 retracts prior to the lower jaw 220. The retraction of the upper jaw 210 toward the upper jaw housing 230 along the angle $\alpha$ will cause the upper lateral clamping surface 214 to approach the lateral outer surface of the mounting structure 122 (e.g., the surface facing away from the opposing surface 206 in the clamped mechanical state of the clamp 200). As the upper jaw 210 is retracted, the clamp body 202 will move vertically downward with respect to the mounting structure 122 until the upper lateral clamping surface 214 abuts the lateral outer surface of the mounting structure 122, laterally capturing the mounting structure 122 between the upper lateral clamping surface 214 and the opposing surface 206. At this position, the upper jaw 210 will no longer retract toward the upper jaw housing 230, and the vertical position of mounting structure 122 with respect to the clamp body 202 will not change.

After translation of the upper jaw 210 is complete and the upper lateral clamping surface 214 abuts the lateral outer surface of the mounting structure 122, continued movement of the arcuate path of the articulable bracket 240 will cause the lower jaw 220 to both travel toward the mounting structure 122 as a result of the arcuate path, and retract with respect to the articulable bracket 240. In a similar manner to the retraction of the upper jaw 210, the arcuate path of the articulable bracket 240 and the retraction of the lower jaw 220 toward the articulable bracket 240 along the angle $\beta$ will cause the lower lateral clamping surface 224 to approach the lateral outer surface of the mounting structure 122, laterally capturing the mounting structure 122 between the lower lateral clamping surface 224 and the opposing surface 206. At this clamped position, as shown in FIGS. 2D and 2F, the lower jaw 220 will no longer retract linearly toward the articulable bracket 240, movement of the articulable bracket 240 by the electric motor 280 will stop, and the clamp 200 will be rigidly clamped to the mounting structure 122. From the clamped position, the clamp 200 can be removed by reversing the electric motor 280 and/or pivoting the manual release lever 250. Optionally, the clamp 200 may include a current sensor in electrical communication with the electric motor 280 to determine the clamp load that can be used to stop rotation of the electric motor 280, detect a loosening of the rod 282, etc. For example, the current sensor may detect an increase or spike in current to indicate that clamping has been successful and to stop continued actuation of the electric motor 280.

FIGS. 3A and 3B are front-right-top and rear-right-top perspective views, respectively, of a modular clamp assembly ("clamp 300") configured in accordance with additional embodiments of the present disclosure. The clamp 300 is configured to be removably attached to a mounting structure such that various components and tools can be mounted to or supported by the clamp 300 and modularly arranged with respect to the mounting structure. In some embodiments, the mounting structure is a rail of the table T shown in FIGS. 1A and 1B, and the clamp 300 is configured to support one or more of the components described above in reference to the first and second manipulator assemblies 130 and 150 (FIG. 1B).

The clamp 300 generally includes a body 302 configured to at least partially surround and protect various components of the clamp 300, provide component positioning and dynamic features, and include one or more accessory mounting locations, among other features. The body 302 may include a distal mounting location 304 configured to couple to other components of the system 100, e.g. the coupling members 142 and 162. In other embodiments, the body 302 includes any number of mounting locations to adapt the clamp 300 for mounting various other components. The body 302 may include other features, such as various slots, a cable receptacle 390 to allow routing of a cable within the body 302, connector mounting features, indices 392 (e.g., indicator lamp, tactile indicators, etc.) to aid in positioning of the clamp 300, etc. The clamp 300 may also include a manual release lever 350 (FIG. 3B) that can be pivoted in the direction of arrow O to release the clamp 300 from the mounting structure. The manual release lever 350 will be explained in greater detail with reference to FIGS. 3C and 3D below.

Routing of the cables through the cable receptacle 390 may allow the clamp 300 to act as a sterile adaptor, with a clean, sterile environment above the clamp 300, and a non-sterile environment below the clamp 300. The cable receptacle 390 may be configured to receive any suitable type of connector, including pass-through, cable-to-cable, pogo pin, intermediate PCB, etc. The cables within the cable receptacle 390 may be data, control, and/or power cables, and can be separated on either side of clamp. In some embodiments, the connectors and/or the cables may be recessed within the body 302 to avoid interfering with other components or staff. In embodiments where the clamp 300 acts as a sterile adapter, an upper end of the clamp 300 may be positioned at the height of the mounting structure 122 or higher, extending into the sterile area, and a lower end of the clamp 300 may be positioned below the mounting structure 122 in the non-sterile area (see, e.g., FIG. 5 of U.S. application Ser. No. 16/408,077, incorporated by reference herein). Although the cable receptacle 390 may not be shown with respect to the other embodiments described herein, the features are suitable for use with any of the embodiments of the present disclosure.

The clamp 300 may include a fixed upper jaw 310 and movable lower jaw 320 configured to interface with a variety of mounting structures (e.g., the mounting structure 122) to couple the clamp 300 to the mounting structure such that, for example, components of the first and second manipulator assemblies 130 and 150 (FIG. 1B) can be arranged and articulated with respect to the mounting structure. The upper jaw 310 may include an upper lateral clamping surface 312 (FIG. 3B) configured to interface with a portion of the mounting structure 122 in a lateral direction (e.g., the Y-direction) when the clamp 300 is clamped on the mounting structure 122, as will be explained in greater detail below. As illustrated, the clamp 300 may include a pair of upper jaws projections 314 (FIG. 3A) in a spaced apart configuration. In other embodiments, the clamp 300 has a continuous upper jaw projection extending across the entire width of the upper jaw, or has any number of jaw segments and/or projections across the width of the upper jaw. The movable lower jaw 320 may project from an articulable bracket 340 to partially enclose the mounting structure 122 in a lateral direction when the clamp 300 is attached to the mounting structure 122. As with the upper jaw 310, in some embodiments, the clamp 300 may include any number of lower jaw segments and/or projections across the width of the lower jaw 320. The lower jaw 320 may be movable with respect to the body 302 by the articulable bracket 340 associated in at least one DOF with the body 302.

FIGS. 3C-3F show cross-sectional right side views of the clamp 300, the cross-sections taken along corresponding positions shown in FIGS. 3A and 3B. In some embodiments, the clamping articulation of the clamp 300 is accomplished by an electric motor 380 (see FIGS. 3E and 3F) that moves the articulable bracket 340 to draw the jaws 310 and 320 toward each other to clamp the mounting structure 122. Referring initially to FIGS. 3C and 3D, the upper jaw 310 includes the upper lateral clamping surface 312 that may be configured to abut an upper corner of the mounting structure 122 during clamping of the clamp 300. The upper lateral clamping surface 312 may be angled with respect to an opposing surface 306 of the body 302 such that the upper lateral clamping surface 312 can accommodate various widths of the mounting structure 122. In this regard, rails with thinner widths would contact the upper lateral clamping surface 312 at a higher position along the upper jaw 310 than rails with thicker widths, which would contact the rail nearer a lower tip of the upper jaw 310.

Similarly, the lower jaw 320 may include a lower lateral clamping surface 322. The lower lateral clamping surface 322 may be configured to abut a lower corner of the mounting structure 122 during engagement of the clamp 300 to the rail. For example, as shown in FIG. 3D, the upper and lower lateral clamping surfaces 314 and 322 may abut the upper and lower corners of the mounting structure 122, respectively, e.g., the corners on the opposite side of the mounting structure 122 away from the opposing surface 306 in the clamped position. As described above with respect to clamp 200, the jaws 210 and 220 of clamp 200 may contact the top, bottom, and two opposite lateral surfaces of the mounting structure 122. In contrast with the clamp 200, the clamp 300 may contact the mounting structure 122 on the upper and lower outer corners of the mounting structure 122 along with a lateral surface of the mounting structure 122 abutting the opposing surface 306. In this regard, the upper and lower lateral clamping surfaces 314 and 322 may capture the mounting structure 122 against the rail opposing surface 306 such that the mounting structure 122 has opposing pressure on both lateral sides when the clamp 300 is attached to the mounting structure 122.

Referring to FIGS. 3C-3F together, the articulable bracket 340 may be movable upward in the Z-direction by the electric motor 380 with respect to the body 302. The articulable bracket 340 may be configured to generally follow a segmented path based on the movement of an upper pin 342 within an upper slot 365 and a lower pin 344 within a lower slot 366. As shown in FIGS. 3C and 3D, the upper slot 365 may have a segmented path with at least a first segment A and a second segment B arranged in different directions. The first and second segments A and B may be linear, may be any suitable shape (e.g., arcuate), may be combined into a single segment, or may be split into more than two segments to create a suitable path of travel of the articulable bracket 340 during clamping of the clamp 300.

Figure 3E:
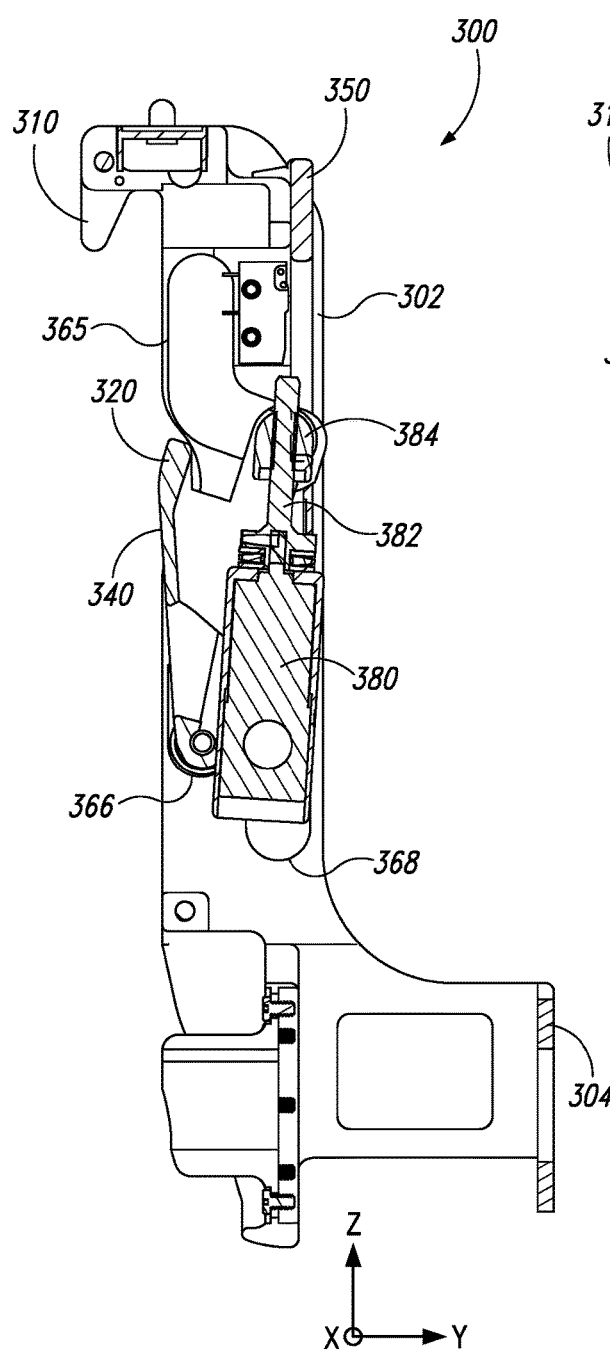
Figure 3F:
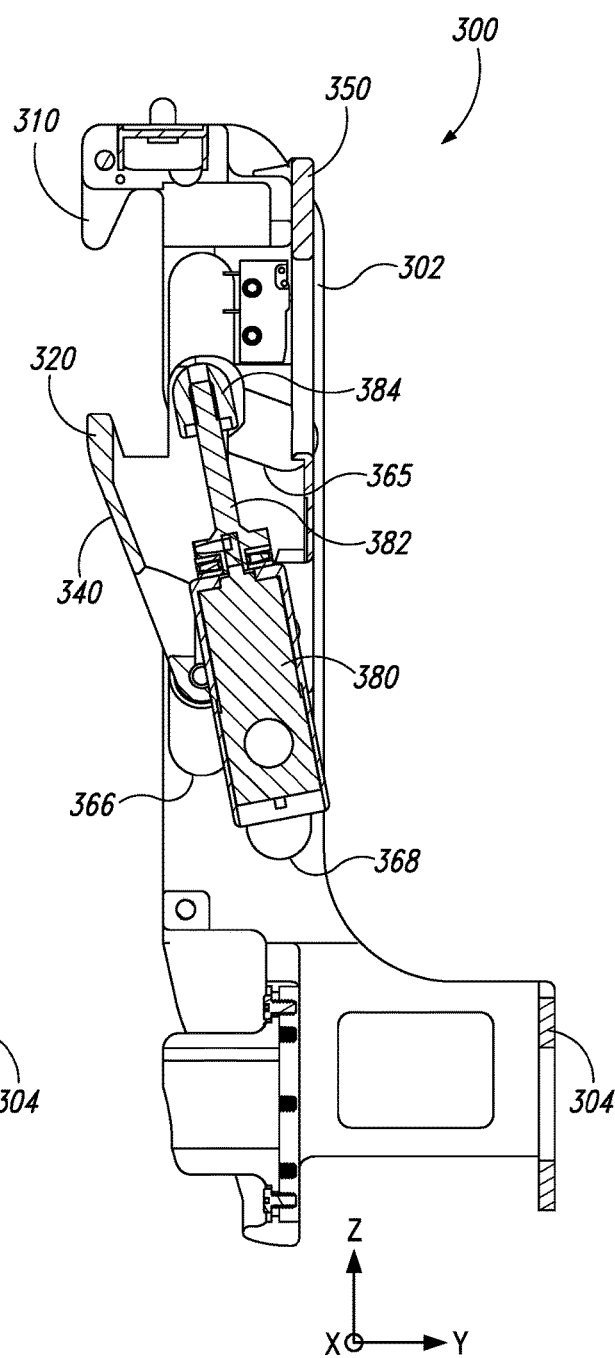

The upper pin 342 may be configured to interface with a translating junction 384 articulable by the electric motor 380 (see FIGS. 3E and 3F). In some embodiments, the translating junction 384 is movable with respect to the electric motor 380 by a rod 382. The rod 382 may be threaded such that rotation of the electric motor 380 advances or retracts the translating junction 384 with respect to the electric motor 380, and thereby effectuate movement of the articulable bracket 340. As shown in FIGS. 3C and 3D, the upper pin 342 may travel within the upper slot 365 and the lower pin 344 may travel within the lower slot 366 during movement of the articulable bracket 340. Referring initially to the position of the articulable bracket 340 in FIG. 3C, the upper pin 342 will generally be positioned in the first segment A of the upper slot 365. As shown, the first segment A is disposed at an angle from the second segment B. The orientation of the first segment A may be configured to move the lower jaw 320 substantially laterally with respect to the opposing surface 306, and pivot about the lower pin 344 as a lower pin 344 travels within the lower slot 366. In other embodiments, the orientation of the first segment A may be any suitable angle with respect to the second segment B.

As shown in the unclamped position of FIG. 3C, when the upper pin 342 is in the furthest position within the first segment A away from the opposing surface 306 and the lower pin 344 is in the lowest position within the lower slot 366, the lower jaw 320 may be generally received within an indentation 308 within the body 302. In this regard, it is possible to retract the articulable bracket 340 such that the lower jaw 320 does not protrude away from the body 302, which may aid in attaching the clamp 300 to the mounting structure 122 prior to clamping (e.g., by providing additional clearance to mount the clamp 300 to rails of different sizes). As the articulable bracket 340 is moved away from the unclamped position in FIG. 3C to the clamped position in FIG. 3D, the upper pin 342 will travel along the first segment A to move the lower jaw 320 laterally outward with respect to the opposing surface 306 until the upper pin 342 reaches the second segment B. As the upper pin 342 travels along the second segment B, the upper pin 342 will generally travel in the same direction as the lower pin 344. In the configuration shown, the articulable bracket 340 will generally initially rotate with respect to the lower pin 344 until the upper pin 342 reaches the second segment B, and then the articulable bracket 340 will generally translate linearly along the opposing surface 306, as the upper pin 342 travels within the second segment B of the upper slot 365 and the lower pin 344 travels within the lower slot 366. In these embodiments, certain of the components of the clamp 300, e.g., the upper and lower slots 365 and 366, the pins 342 and 344, etc. may be positioned on either side of the clamp 300 in the X-direction (e.g. in pairs), such that a plurality of these components are used to articulate the clamp 300 during clamping to the mounting structure 122. In other embodiments, components illustrated as having two or more instances, may be used with a single instance, or more instances than illustrated herein, and are within the scope of the present disclosure.

As mentioned above, the manual release lever 350 may be used to override the clamped state (FIG. 3C) of the clamp 300 by pivoting the manual release lever 350 about a pivot 358 away from the body 302 in the direction of arrow O. As the manual release lever 350 is pivoted away from the body 302, a locking pin 352 releases from a catch 354, allowing the articulable bracket 340 to move from the position in FIG. 3C (clamped) to the position in FIG. 3D (unclamped). When the locking pin 352 is released from the catch 354, a manual release pin 356 may be configured to travel within a manual release slot 368, moving the articulable bracket 340 downward and away from the mounting structure 122 to release the rail from the clamp 300.

With reference to FIGS. 3C-3F, movement of the components of the clamp 300 during one representative embodiment of clamping to a mounting structure 122 will now be described in greater detail. Initially referring to the unclamped state shown in FIG. 3C, the clamp 300 will initially be placed on the mounting structure 122 by interfacing the upper jaw 310 with the mounting structure 122. In this configuration, the opposing surface 306 will contact the lateral surface of the mounting structure 122 facing the opposing surface 306, and the upper lateral clamping surface 312 will contact an upper corner of the mounting structure 122. As the clamp 300 is placed on the rail, one or more sensors (not shown) on the clamp 300 may detect the rail and automatically initiate clamping of the clamp 300. In other embodiments, a user, system, processor, etc. may initiate an automated or manual clamping operation of the clamp 300.

As also shown in FIGS. 3C and 3E, in the unclamped position, the articulable bracket 340 is positioned downward away from the mounting structure 122. In this configuration, the opening between the upper and lower jaws 310 and 320 may be maximized, and the lower jaw 320 may be retracted within the indentation 308 to allow greater ingress of the mounting structure 122 between the upper and lower jaws 310 and 320. As the electric motor 380 moves the translating junction 384 upward, the upper pin 342 travels along the first segment A toward the second segment B to substantially rotate the articulable bracket 340 about the lower pin 344. During such movement along the first segment A, the lower pin 344 may have some component of movement within the lower slot 366. However, in the illustrated embodiment, the movement of the lower pin 344 within the lower slot 366 will generally be smaller than the movement of the upper pin 342 within the first segment A, substantially resulting in a rotation of the articulable bracket 340 as opposed to a translation.

For an initial portion of the movement of the jaws 310 and 320, the lower jaw 320 moves laterally outward away from the opposing surface 306 in the negative Y-direction. At a point where the upper pin 342 reaches the second segment B of the upper slot 365, the rotation of the articulable bracket 340 will stop and further translation of the translating junction 384 will cause the articulable bracket 340 to move upward toward the mounting structure 122 in the Z-direction. As the articulable bracket 340 continues upward along the path of the second segment B and the lower slot 366, the lower lateral clamping surface 322 will abut a lower corner of the mounting structure 122, in a position shown in FIGS.

3C and 3E, where movement of the articulable bracket 340 by the electric motor 380 will stop, and the clamp 300 will be rigidly clamped to the mounting structure 122. The clamp 300 may include a current sensor in electrical communication with the electric motor 380 to determine the clamp load that can be used to stop rotation of the electric motor 380, detect a loosening of the rod 382, etc. From the clamped position, the clamp 300 can be removed by reversing the electric motor 380 and/or pivoting the manual release lever 350.

Figure 4A:
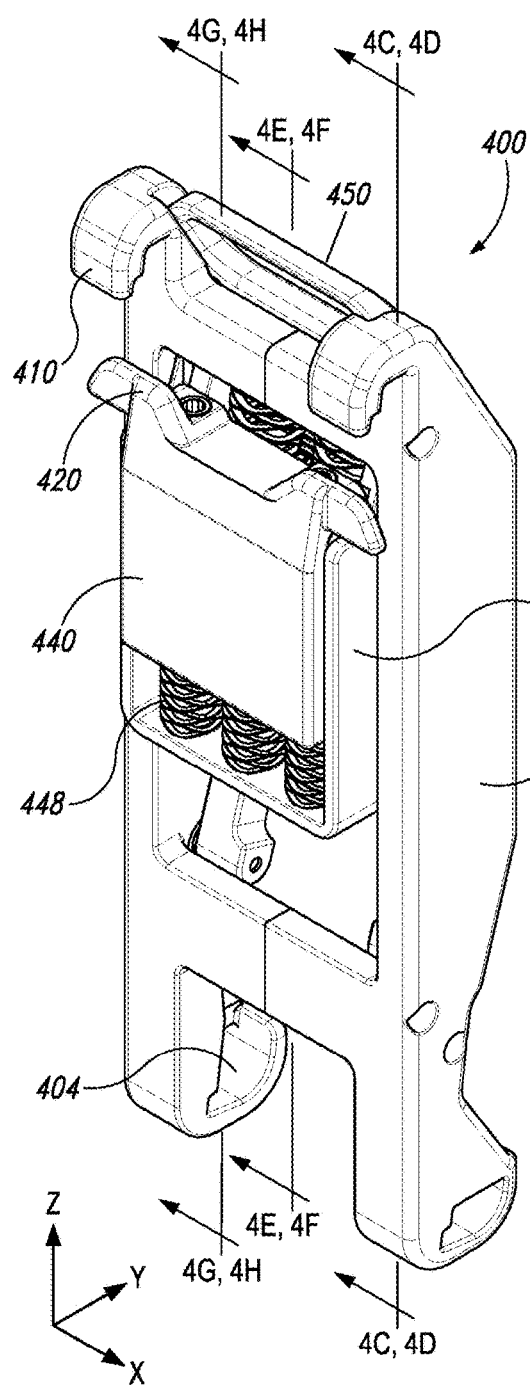
FIGS. 4A and 4B are front-right-top and rear-right-top perspective views, respectively, of a modular clamp assembly configured in accordance with embodiments of the present disclosure.
Figure 4B:
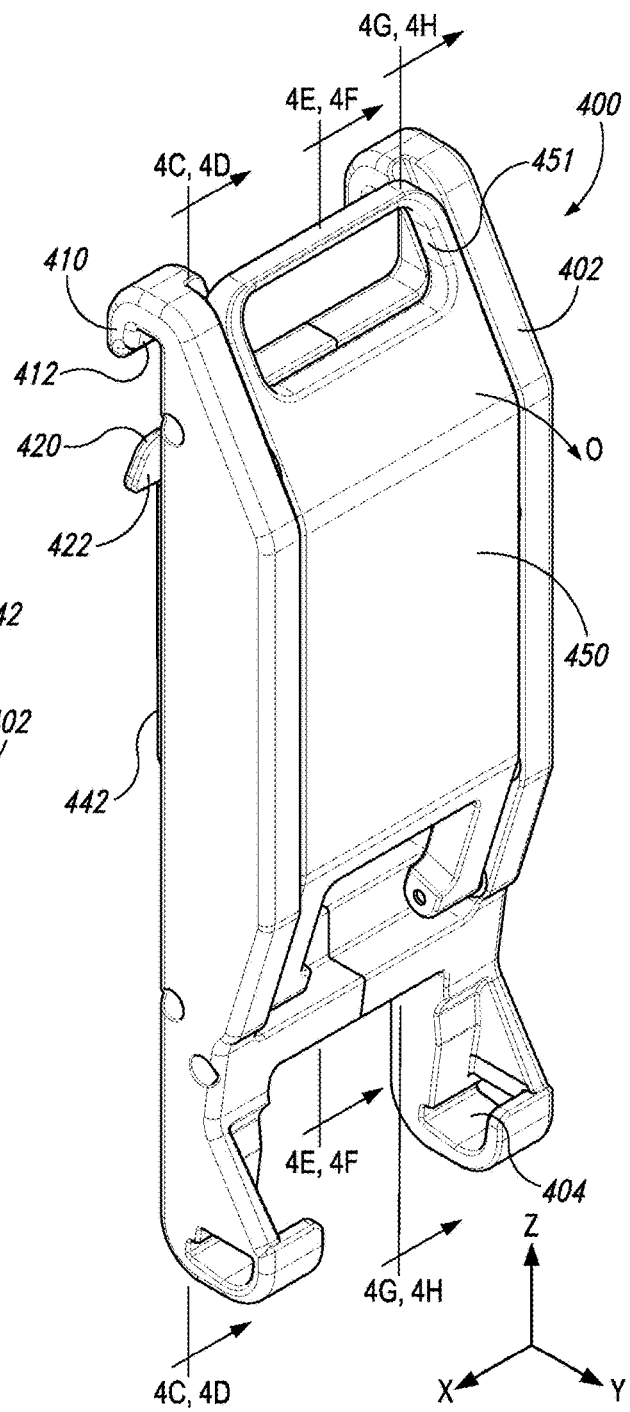

FIGS. 4A and 4B are front-right-top and rear-right-top perspective views, respectively, of a modular clamp assembly ("clamp 400") configured in accordance with additional embodiments of the present disclosure. In contrast with the clamps 200 and 300 described above with reference to FIGS. 2A-3F, the clamp 400 may be configured to clamp to the mounting structure 122 by manual articulation, as opposed to articulation by an electrical motor. The clamp 400 is configured to be removably attached to a structure such that various components and tools can be modularly arranged with respect to the structure. In some embodiments, the structure is the table T shown in FIGS. 1A and 1B, and the clamp 400 is configured to support one or more of the components described above in reference to the first and second manipulator assemblies 130 and 150 (FIG. 1B).

The clamp 400 generally includes a body 402 configured to at least partially surround and protect various components of the clamp 400, provide component positioning and dynamic features, and include one or more accessory mounting locations, among other features. The body 402 may include a distal mounting location 404 configured to couple to other components of the system 100, e.g., the coupling members 142 and 162. In other embodiments, the body 402 includes any number of mounting locations to adapt the clamp 400 for mounting various other components. The body 402 may include other features, such as various slots, connector mounting features, indices (e.g., indicator lamp, tactile indicators, etc.) to aid in positioning of the clamp, etc. The clamp 400 may also include a lever 450 with a handle portion 451 (FIG. 4B) that can be pivoted in the direction of arrows CL and O to clamp and/or release the clamp 400, respectively, from the mounting structure, as will be explained in greater detail below.

As noted above with respect to clamp 300, use of the clamp 400 may include routing of one or more cables through a cable receptacle (e.g., the cable receptacle 390 of the clamp 300 shown in FIGS. 3A and 3B may be suitable for use with the clamp 400), and may allow the clamp 400 to act as a sterile adaptor, with a clean, sterile environment above the clamp 400, and a non-sterile environment below the clamp 400. Such cable receptacles may be configured to receive any suitable type of connector, including passthrough, cable-to-cable, pogo pin, intermediate PCB, etc. The cables within the cable receptacle may be data, control, and/or power cables, and can be separated on either side of clamp. In some embodiments, the connectors and/or the cables may be recessed within the body 402 to avoid interfering with other components or staff. In embodiments where the clamp 400 acts as a sterile adapter, an upper end of the clamp 400 may be positioned at the height of the mounting structure 122 or higher, extending into the sterile area, and a lower and of the clamp 400 may be positioned below the mounting structure 122 in the non-sterile area.

The clamp 400 may include a fixed upper jaw 410 and movable lower jaw 420 configured to interface with a variety of mounting structures (e.g., the mounting structure 122) to couple the clamp 400 to the mounting structure such that, for example, components of the first and second manipulator assemblies 130 and 150 (FIG. 1B) can be arranged and articulated with respect to the mounting structure. The upper jaw 410 may include an upper lateral clamping surface 412 (FIG. 4B) configured to interface the mounting structure 122 in a lateral direction when the clamp 400 is clamped on the mounting structure 122, as will be explained in greater detail below. As illustrated, the clamp 400 may include a pair of upper jaws 410 (FIG. 4A) in a spaced apart configuration. In other embodiments, the clamp 400 has a continuous upper jaw extending across the entire width of the upper jaw, or has any number of jaw segments and/or projections across the width of the upper jaw. The movable lower jaw 420 may project from an articulable bracket 440 movable with respect to a carriage 442 such that the lower jaw 420 is movable to partially enclose the mounting structure 122 in a lateral direction when the clamp 400 is clamped on the mounting structure 122. As with the upper jaw 410, in some embodiments, the clamp 400 may include any number of lower jaw segments and/or projections across the width of the lower jaw 420. The lower jaw 420 may be movable with respect to the body 402 by the articulable bracket 440 and the carriage 442 associated in at least one DOF with the body 402.

Figures 4C, 4D:
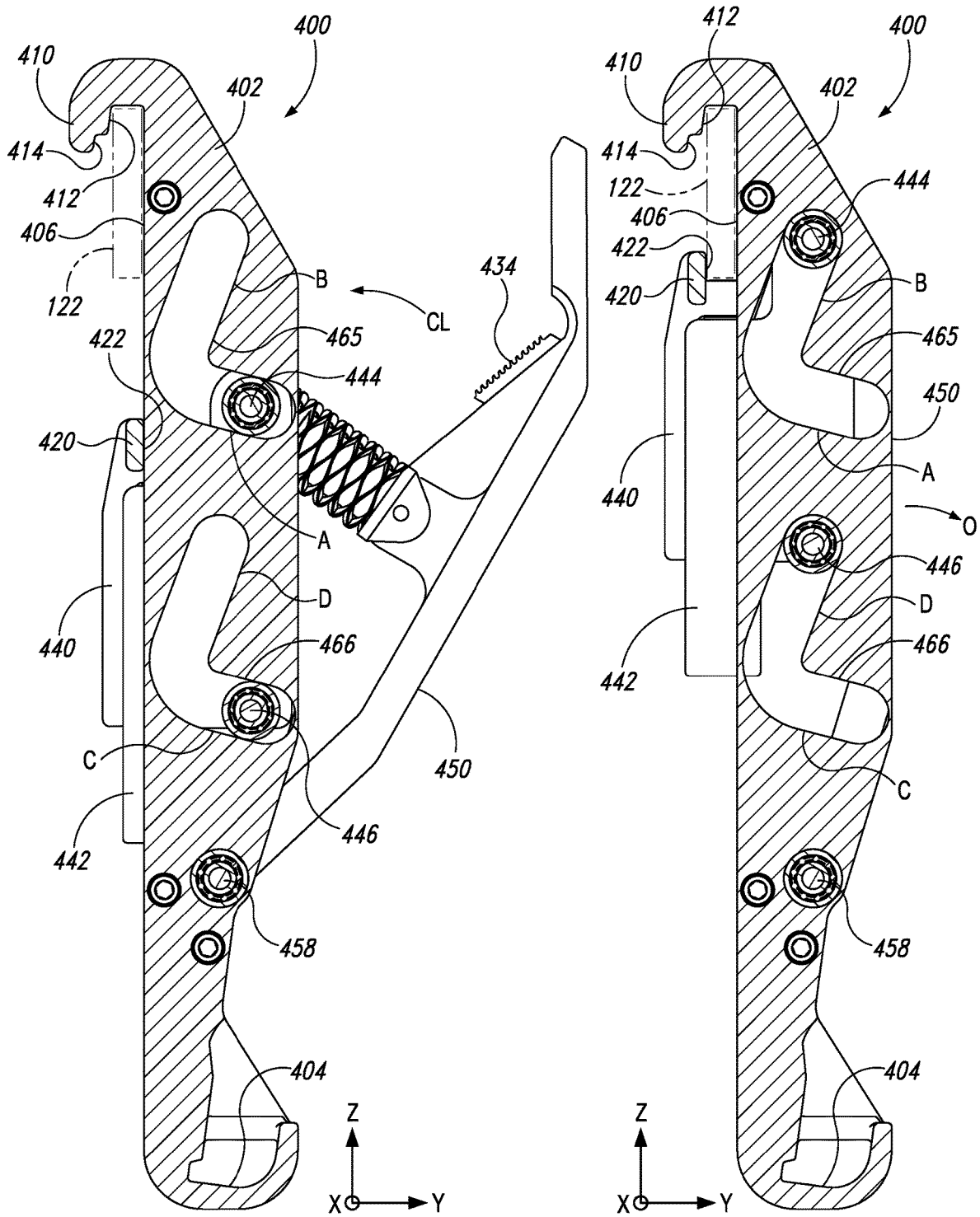
FIGS. 4C-4H are cross-sectional right side views of the modular clamp assembly of FIGS. 4A and 4B, with the cross-sections taken along corresponding positions shown in FIGS. 4A and 4B.

FIGS. 4C-4H show cross-sectional right side views of the clamp 400, the cross-sections taken along corresponding positions shown in FIGS. 4A and 4B. In some embodiments, the clamping articulation of the clamp 400 is accomplished by rotating the lever 450 (compare FIGS. 4C, 4E, and 4G with 4D, 4F, and 4H, respectively) that moves the carriage 442 to draw the jaws 410 and 420 together to clamp the mounting structure 122. Referring initially to FIGS. 4C and 4D, the upper jaw 410 includes the first upper lateral clamping surface 412 and a second upper lateral clamping surface 414 that may be configured to abut a portion (e.g., a lateral surface, an upper corner, etc.) of the mounting structure 122 during clamping of the clamp 400. The upper lateral clamping surfaces 412 and 414 may be angled or notched with respect to an opposing surface 406 of the body 402 such that the upper lateral clamping surfaces 412 and 414 can accommodate various widths of the mounting structure 122. In this regard, rails with thinner widths can contact the first upper lateral clamping surface 412 and a higher position along the opposing surface 406 than rails with thicker widths, which would contact the second upper lateral clamping surface 414 nearer a tip of the upper jaw 410.

Similarly, the lower jaw 420 may include a lower lateral clamping surface 422. The lower lateral clamping surface 422 may be configured to abut a lower corner of the mounting structure 122 during clamping of the clamp 400. As shown in FIG. 4D, the upper and lower lateral clamping surfaces 412, 414, and 422 may abut one or more of the lateral surface or upper and lower corners of the mounting structure 122, e.g., the corners positioned away from the opposing surface 406 in the clamped position. In contrast to the clamp 200, the clamp 400 may contact the mounting structure 122 on a lateral surface abutting the opposing surface 406 and the upper and lower outer corners and/or the lateral surface of the mounting structure 122 opposite the opposing surface 406. In this regard, the upper and lower lateral clamping surfaces 412, 414, and 422 may capture the mounting structure 122 against the rail opposing surface 406 such that the mounting structure 122 has opposing pressure on both lateral sides when the clamp 400 is clamped.

Referring to FIGS. 4C-4H together, the articulable bracket 440 and the carriage 442 may be movable by the lever 450 with respect to the body 402. The articulable bracket 440 in the carriage 442 may be configured to move with respect to each other during clamping of the clamp 400. In some embodiments, the movement of the articulable bracket 440 with respect to the carriage 442 may be biased by a biasing member 448 (see FIGS. 4A, 4E, and 4F). As will be explained in greater detail below, the biasing member 448 may be configured to allow constrained movement of the articulable bracket 440 with respect to the carriage 442 to accommodate differing heights of the mounting structure 122.

During rotation of the lever 450 in the direction of arrow O, the carriage 442 may be configured to generally follow a segmented arcuate path based on the movement of an upper pin 444 within an upper slot 465 and a lower pin 446 within a lower slot 466. As shown in FIGS. 4C and 4D, the upper slot 465 may have a segmented path with at least a first segment A and a second segment B arranged in different directions, and the lower slot 466 may have a segmented path with at least a third segment C and a fourth segment D arranged in different directions. The first and second segments A and B may be substantially linear, may be any suitable shape (e.g., arcuate), may be combined into a single segment, or may be split into more than two segments to create a suitable path of travel of the carriage 442 during clamping of the clamp 400. Likewise, the third and fourth segments C and D may be substantially linear, may be any suitable shape (e.g., arcuate), may be combined into a single segment, or may be split into more than two segments to create a suitable path of travel of the carriage 442 during clamping of the clamp 400. In the illustrated embodiments, the upper and lower slots 465 and 466 have substantially the same length, orientation, and configuration. However, in other embodiments, the upper and lower slots 465 and 466 may have any suitable length, orientation, and configuration, and in these regards may differ between each other. As shown, the transition between the first and second segments A and B and between the third and fourth segments C and D may have an arcuate shape to smoothly transition the motion of the articulable bracket 440 and the carriage 442 as it transitions from travel within the second and fourth slots B and D to the first and third slots A and C during clamping of the clamp 400.

As shown in FIGS. 4C and 4D, the upper pin 444 may travel within the upper slot 465 and the lower pin 446 may travel within the lower slot 466 during movement of the articulable bracket 440 and the carriage 442. Referring initially to the position of the articulable bracket 440 and the carriage 442 in FIG. 4C, the upper pin 444 will generally be positioned in the first segment A of the upper slot 465, and the lower pin 446 will generally be positioned in the third segment C of the lower slot 466. As shown, the first segment A is disposed at an angle from the second segment B and the third segment C is disposed at an angle from the fourth segment D. In other embodiments, the orientation of the first segment A may be any suitable angle with respect to the second segment B, and the orientation of the third segment C may be any suitable angle with respect to the fourth segment D.

The first and third segments A and C may control the travel of the articulable bracket 440 and the carriage 442 from the unclamped position (FIG. 4C) as the clamp 400 articulates to the clamped position (FIG. 4D). The orientations of the first and third segments A and C have a majority directional component in the horizontal Y-direction (as viewed in FIGS. 4C and 4D), with a minor directional component in the vertical Z-direction. Such orientations will cause the lower jaw 420 to translate substantially outward in the negative Y-direction, clearing the bottom surface of the mounting structure 122, with a minor amount of translation in the Z-direction. As the upper pin 444 and the lower pin 446 transition from the first and third segments A and C to the second and fourth segments B and D, the direction of travel of the articulable bracket 440 and the carriage 442 will change based on the orientation of the second and fourth segments B and D. In this regard, the orientations of the second and fourth segments B and D have a majority directional component in the vertical Z-direction, with a minor directional component in the horizontal Y-direction. Such orientations will cause the lower jaw 420 to translate substantially upward in the Z-direction, toward the bottom surface of the mounting structure 122, with a minor amount of translation in the Y-direction such that the lower lateral clamping surface 422 translates toward the lateral surface of the mounting structure 122.

As shown in the unclamped position of FIG. 4C, when the upper pin 444 is in the furthest position within the first segment A away from the opposing surface 406 and the lower pin 446 is also in the furthest position within the third segment C away from the opposing surface 406, the lower jaw 420 may generally be positioned immediately adjacent to or abutting the body 402. In this regard, it is possible to retract the articulable bracket 440 and the carriage 442 such that the lower jaw 420 minimally protrudes away from the body 402, which may aid in attaching the clamp 400 to the mounting structure 122 prior to clamping. In other embodiments, the body 402 may have an indentation or recess (not shown) configured to receive the lower jaw 420 (see, e.g., the indentation 308 in FIG. 3C) such that the lower jaw 420 may be positioned to not protrude from the body 402, to provide additional clearance for mounting the clamp 400 to mounting structures of different sizes. As described above, the lever 450 may be used to transition the clamp 400 between the clamped and unclamped positions by pivoting the lever 450 about a pivot 458 away from the body 402 in the direction of arrow O. As the lever 450 is pivoted away from the body 402, a lever pin 476 begins to generally translate in the Y-direction, and eventually allows the articulable bracket 440 and the carriage 442 to move from the position in FIG. 4D (clamped) to the position in FIG. 4C (unclamped). The lever pin 476 may use an over-center locking design, as will be explained in greater detail below.

With reference to FIGS. 4C-4H, the movement of the components of the clamp 400 during one representative embodiment of clamping to a mounting structure 122 will now be described in greater detail. Initially referring to the unclamped state shown in FIGS. 4C, 4E, and 4G, the clamp 400 will initially be placed on the mounting structure 122 by interfacing the upper jaw 410 with the mounting structure 122. In this configuration, the opposing surface 406 will contact the lateral surface of the mounting structure 122 facing the opposing surface 406, and one or both of the upper lateral clamping surfaces 412 and 414 will contact at least an upper corner of the mounting structure 122.

When the lever 450 is rotated in a direction of arrow CL as shown in FIG. 4C, the lever pin 476 is pivoted with the lever 450 about the pivot 458, and may therefore follow an arcuate path away from the opposing surface 406. The lever pin 476 may be operably coupled to a translating junction 484 through a telescoping piston assembly 452 configured to extend and retract such that the lever pin 476 and the translating junction 484 are movable with respect to each other during clamping of the clamp 400. The translating junction 484 may be coupled to the upper pin 444 such that the translating junction 484 travels along the path of the upper slot 465 through the movement of the lever 450. The telescoping piston assembly 452 may be dampened and/or biased (e.g., with a biasing member 432 surrounding the telescoping piston assembly 452) such that movement of the lever pin 476 with respect to the translating junction 484 is restricted.

Figure 4E:
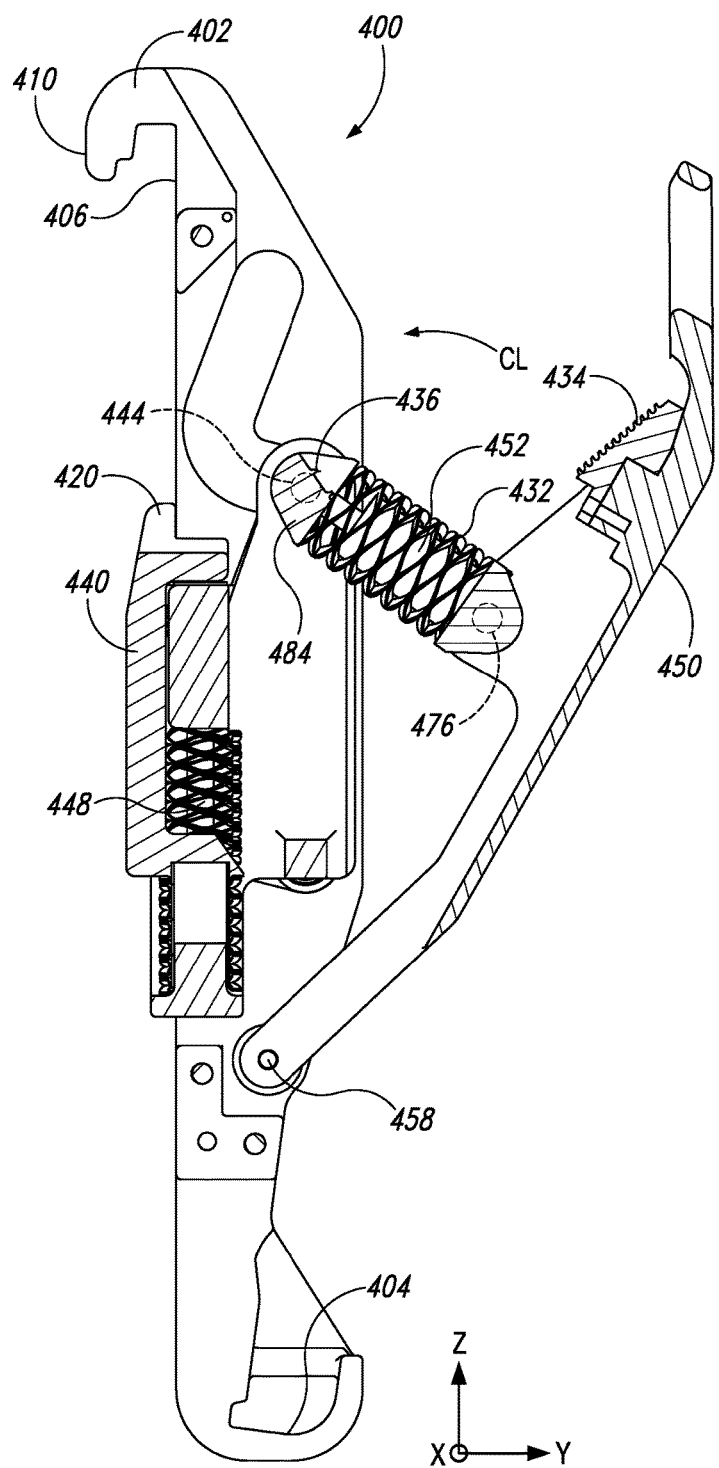
Figure 4F:
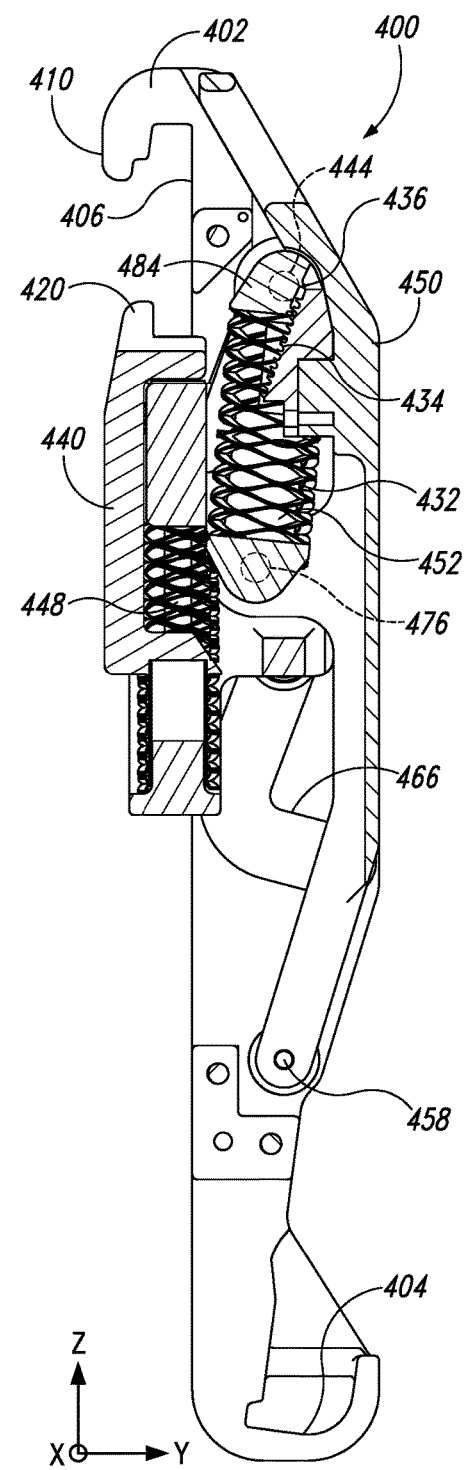

The damping and/or biasing of the telescoping piston assembly 452 may aid in clamping of the clamp 400 onto the mounting structure 122 and provide a force to hold the lever 450 against the body 402 in the clamped position using the over-center configuration shown in FIG. 4F. As shown, when the lever 450 is in the closed/clamped position, the lever pin 476 is positioned closer to the opposing surface 406 than a straight line extending through a central axis of the lever pivot 458 and a central axis of the upper pin 444 (e.g., the lever pin 476 is positioned on the side of the line toward the negative Y-direction). In this configuration, the line extending through the lever pivot 458 and the upper pin 444 represents the direction of the force applied by the biasing member 432 tending to separate the translating junction 484 from the lever pin 476. As a result of the position of the lever pin 476 in the over-center configuration, the lever 450 is biased toward the closed position until the lever 450 is rotated in the direction of arrow O such that the lever pin 476 is positioned further from the opposing surface 406 than a straight line connecting the lever pivot 458 and the upper pin 444 (e.g., the lever pin 476 crosses the line to the side of the line in the positive Y-direction). In other embodiments, the lever 450 may have a detent, a manual lock, or other suitable retention feature to keep the clamp 400 in the clamped position until removal.

In embodiments of the clamp 400, certain of the components, e.g., the upper and lower slots 465 and 466, the pins 444 and 446, the telescoping piston assembly 452, etc. may be positioned on either side of the clamp 400 in the X-direction (e.g., in pairs), such that a plurality of these components are used to articulate the clamp 400 during clamping to the mounting structure 122. In other embodiments, components illustrated as having two or more instances, may be used with a single instance, or more instances than illustrated herein, and are within the scope of the present disclosure.

Figure 4G:
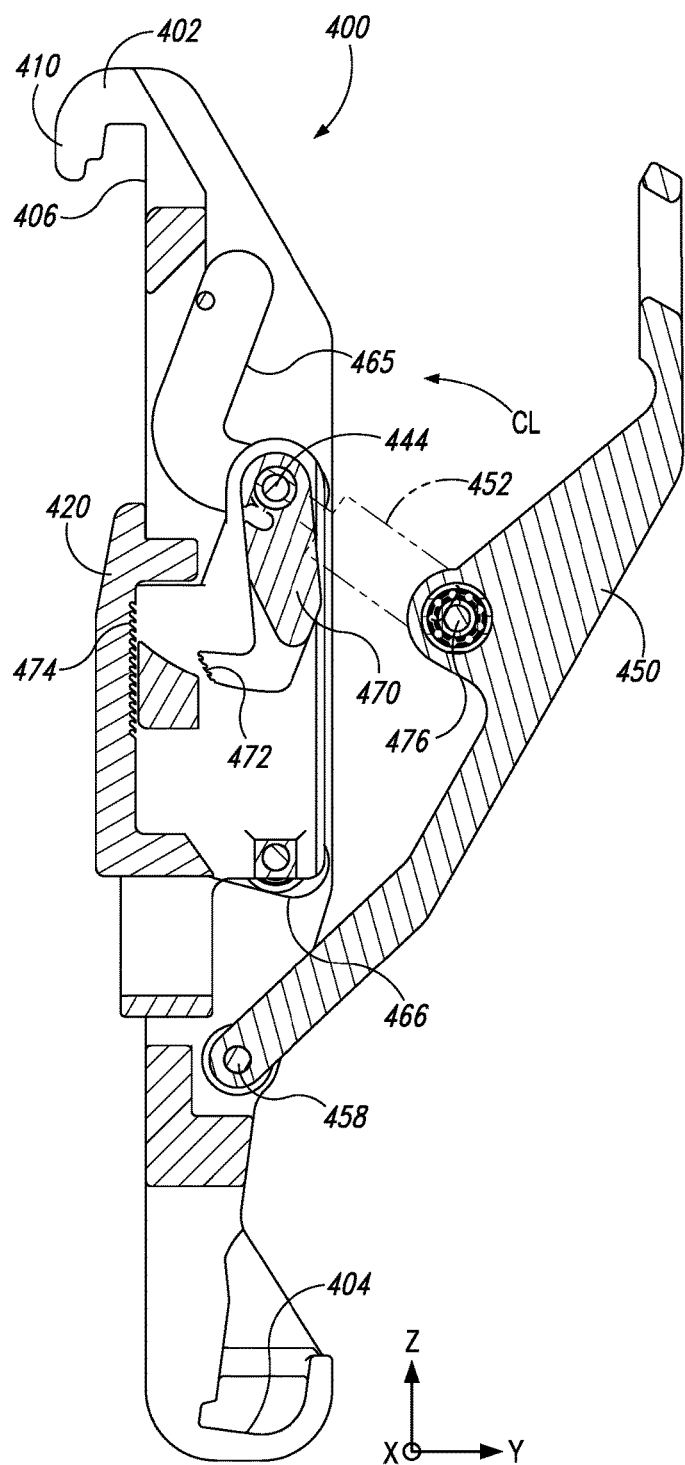

As also shown in FIGS. 4C, 4E, and 4G, in the unclamped position, the articulable bracket 440 and the carriage 442 are positioned downward away from the mounting structure 122 (see FIG. 4C). In this configuration, the opening between the upper and lower jaws 410 and 420 may be maximized, and the lower jaw 420 may be adjacent to the body 402 or optionally retracted within an indentation to allow ingress of the mounting structure 122 between the upper and lower jaws 410 and 420. As the lever 450 rotates in a direction of arrow CL, the translating junction 484 and the upper pin 444 travel along the first segment A toward the second segment B and the lower pin 446 travels along the third segment C toward the fourth segment D to substantially translate the articulable bracket 440 and the carriage 442 in the direction of the first and third segments A and C.

For an initial portion of such movement, the lower jaw 420 translates in the negative Y-direction away from the body 402 with a minority component upward in the Z-direction toward the mounting structure 122. At the transition point where the upper pin 444 reaches the second segment B of the upper slot 465 and the lower pin 446 reaches the fourth segment D of the lower slot 466, the direction of translation of the articulable bracket 440 and the carriage 442 will transition to translation in the Z-direction toward the bottom surface of the mounting structure 122 with a minority component laterally inward in the Y-direction toward the lateral surface of the mounting structure 122. As the articulable bracket 440 and the carriage 442 continues upward along the path of the second and fourth segments B and D. When the lower jaw 420 contacts the bottom surface of the mounting structure 122, the lower lateral clamping surface 422 may not yet be in contact with the lateral surface of the mounting structure 122 four clamping of the clamp 400. As described above, the movement of the articulable bracket 440 with respect to the carriage 442 may be biased by the biasing member 448. As the lever 450 continues to be rotated to the closed position, the articulable bracket 440 will no longer move upward in the Z-direction and further upward movement of the carriage 442 will compress the biasing member 448. This continued movement will only have a component in the Y-direction drawing the lower lateral clamping surface 422 toward the lateral surface of the mounting structure 122.

After further rotation of the lever 450, the lower lateral clamping surface 422 will abut the lateral surface of the mounting structure 122, as shown in FIG. 4D. When the lower jaw 420 and the lower lateral clamping surface 422 are in contact with the mounting structure 122, the lower jaw 420 will no longer move with respect to the mounting structure 122, and the biasing members 432 and 448 will continue to compress as the lever 450 is rotated to the closed position abutting the body 402. At this state, it may be desirable to lock the articulable bracket 440 and the carriage 442 with respect to each other, and the translating junction 484 and the lever pin 476 with respect to each other. Referring to FIGS. 4E and 4F, one embodiment of a toothed interface locking mechanism for the translating junction 484 and the lever pin 476 is shown. A portion of the lever 450 may include teeth 434 protruding from a surface of the lever 450 and configured to contact a portion of the translating junction 484 when the lever 450 is in the closed position, as shown in FIG. 4F. Correspondingly, the translating junction 484 may include teeth 436 configured to interface with the teeth 434 of the lever 450 to lock the translating junction 484 with respect to the lever pin 476. By locking the components, the clamp 400 may be configured to withstand greater loads.

Figure 4H:
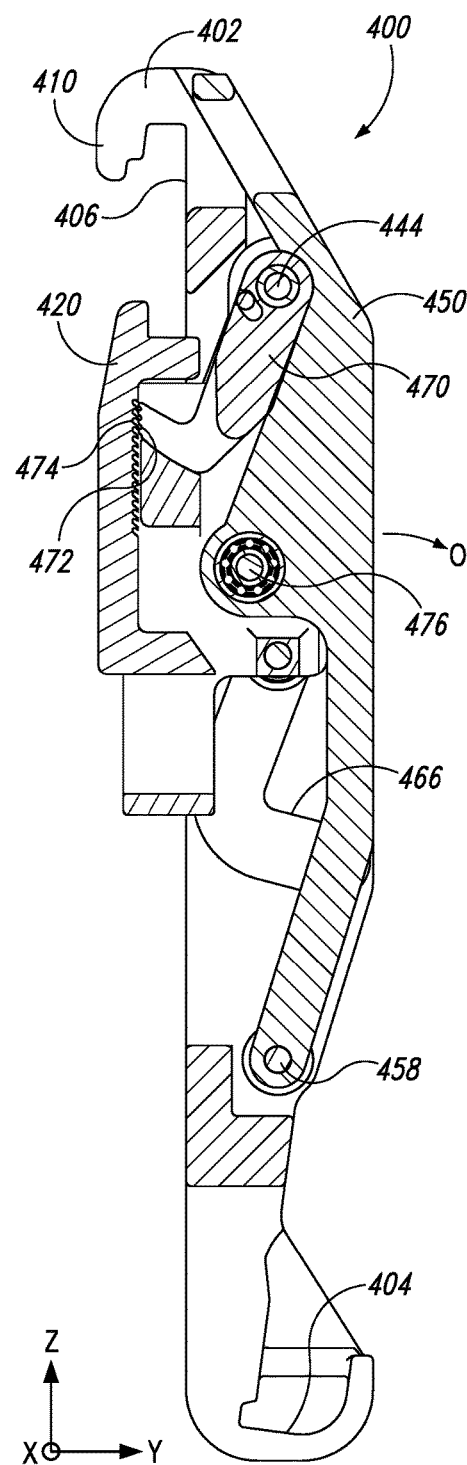

Referring now to FIGS. 4G and 4H, one embodiment of a locking mechanism for the articulable bracket 440 and the carriage 442 is shown. The upper pin 444 may include a rotatable arm 470 configured to interface with the lever 450 as the lever approaches the closed position. In this regard, the rotatable arm 470 may be biased away from the locked position, described below, until the lever 450 contacts the rotatable arm 470 and rotates the rotatable arm 470 toward the locked position. The rotatable arm 470 may include teeth 472 positioned at an end of the rotatable arm 470 and configured to contact teeth 474 positioned on the articulable bracket 440 to lock the articulable bracket 440 with respect to the carriage 442. As the lever 450 rotates the rotatable arm 470, the teeth 472 of the rotatable arm 470 engage with the teeth 474 of the articulable bracket 440 and lock the components. By locking the components, the clamp 400 may be configured to withstand greater loads. The clamp 400 may be removed from the mounting structure 122 by rotating the lever 450 in the direction of arrow O (see FIGS. 4D, 4F, and 4H), in which the movement of the components of the clamp 400 described above will be substantially reversed.

Figure 5A:
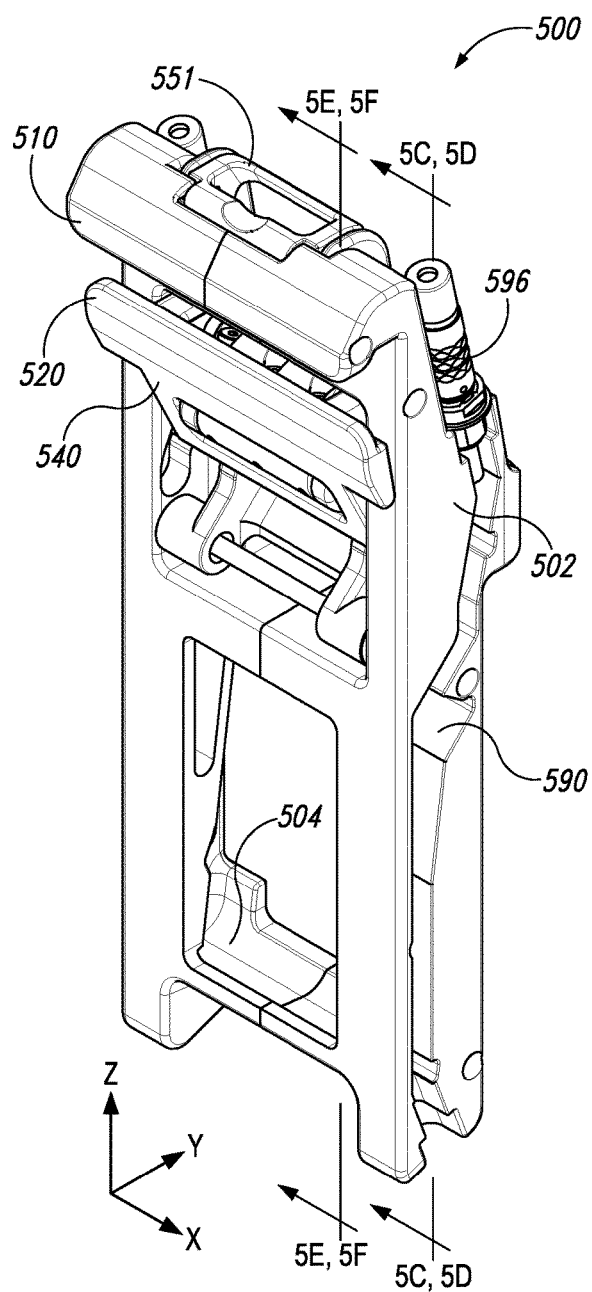
FIGS. 5A and 5B are front-right-top and rear-right-top perspective views, respectively, of a modular clamp assembly configured in accordance with embodiments of the present disclosure.
Figure 5B:
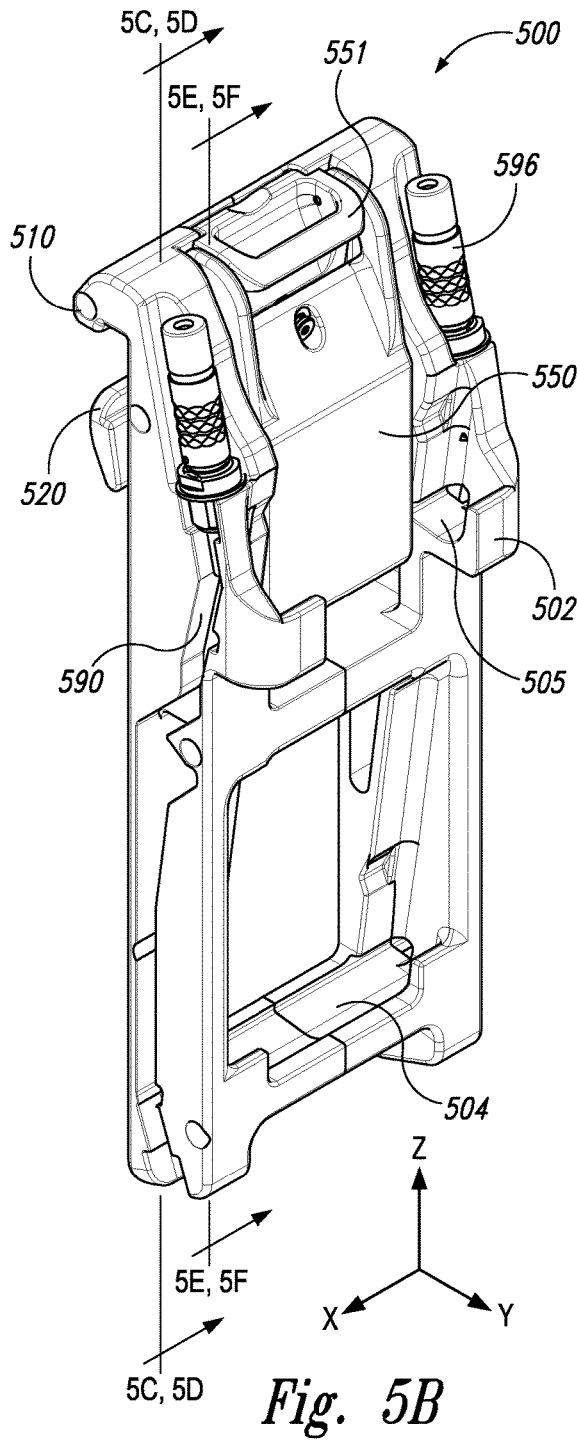

FIGS. 5A and 5B are front-right-top and rear-right-top perspective views, respectively, of a modular clamp assembly ("clamp 500") configured in accordance with additional embodiments of the present disclosure. The clamp 500 is configured to be removably attached to a structure such that various components and tools can be modularly arranged with respect to the structure. In some embodiments, the structure is the table T shown in FIGS. 1A and 1B, and the clamp 500 is configured to support one or more of the components described above in reference to the first and second manipulator assemblies 130 and 150 (FIG. 1B).

The clamp 500 generally includes a body 502 configured to at least partially surround and protect various components of the clamp 500, provide component positioning and dynamic features, and include one or more accessory mounting locations, among other features. The body 502 may include a distal mounting location 504 configured to couple to other components of the system 100, e.g. the coupling members 142 and 162. In other embodiments, the body 502 includes any number of mounting locations, such as an intermediate mounting location 505 (FIG. 5B), to adapt the clamp 500 for mounting various other components. The body 502 may include other features, such as various slots, such as a cable receptacle 590 to allow routing of a cable within the body 502, connector mounting features for a connector 596, such as a connector cavity 598, indices (e.g., indicator lamp, tactile indicators, etc.) to aid in positioning of the clamp 500, etc. The clamp 500 may also include a lever 550 with a handle portion 551 (FIG. 5B) that can be pivoted in the direction of arrows CL and O to clamp and/or release the clamp 500, respectively, from the mounting structure, as will be explained in greater detail below.

Routing of the cables through the cable receptacle 590 using connectors 596 may allow the clamp 500 to act as a sterile adaptor, with a clean, sterile environment above the clamp 500, and a non-sterile environment below the clamp 500. Such cable receptacles 590 may be configured to receive any suitable type of connector 596, including pass-through, cable-to-cable, pogo pin, intermediate PCB, etc. The cables within the cable receptacle may be data, control, and/or power cables, and can be separated on either side of the clamp. In some embodiments, the connectors and/or the cables may be recessed within the body 502 to avoid interfering with other components or staff. In embodiments where the clamp 500 acts as a sterile adapter, an upper end of the clamp 500 may be positioned at the height of the mounting structure 122 or higher, extending into the sterile area, and a lower end of the clamp 500 may be positioned below the mounting structure 122 in the non-sterile area.

The clamp 500 may include a fixed upper jaw 510 and movable lower jaw 520 configured to interface with a variety of mounting structures (e.g., the mounting structure 122) to couple the clamp 500 to the mounting structure such that, for example, components of the first and second manipulator assemblies 130 and 150 can be arranged and articulated with respect to the mounting structure. The upper jaw 510 may include an upper lateral clamping surface 512 (see FIG. 5C) configured to interface the mounting structure 122 in a lateral direction when the clamp 500 is clamped on the mounting structure 122, as will be explained in greater detail below. As illustrated, the clamp 500 may include a continuous upper jaw 510 (FIG. 5A). In other embodiments, the clamp 500 has any number of jaw segments and/or projections across the width of the upper jaw. The movable lower jaw 520 may project from an articulable bracket 540 movable with respect to the body 502 such that the lower jaw 520 is movable to partially enclose the mounting structure 122 in a lateral direction when the clamp 500 is clamped on the mounting structure 122. As with the upper jaw 510, in some embodiments, the clamp 500 may include any number of lower jaw segments and/or projections across the width of the lower jaw 520. The lower jaw 520 may be movable with respect to the body 502 by the articulable bracket 540 associated in at least one DOF with the body 502.

Figure 5C:
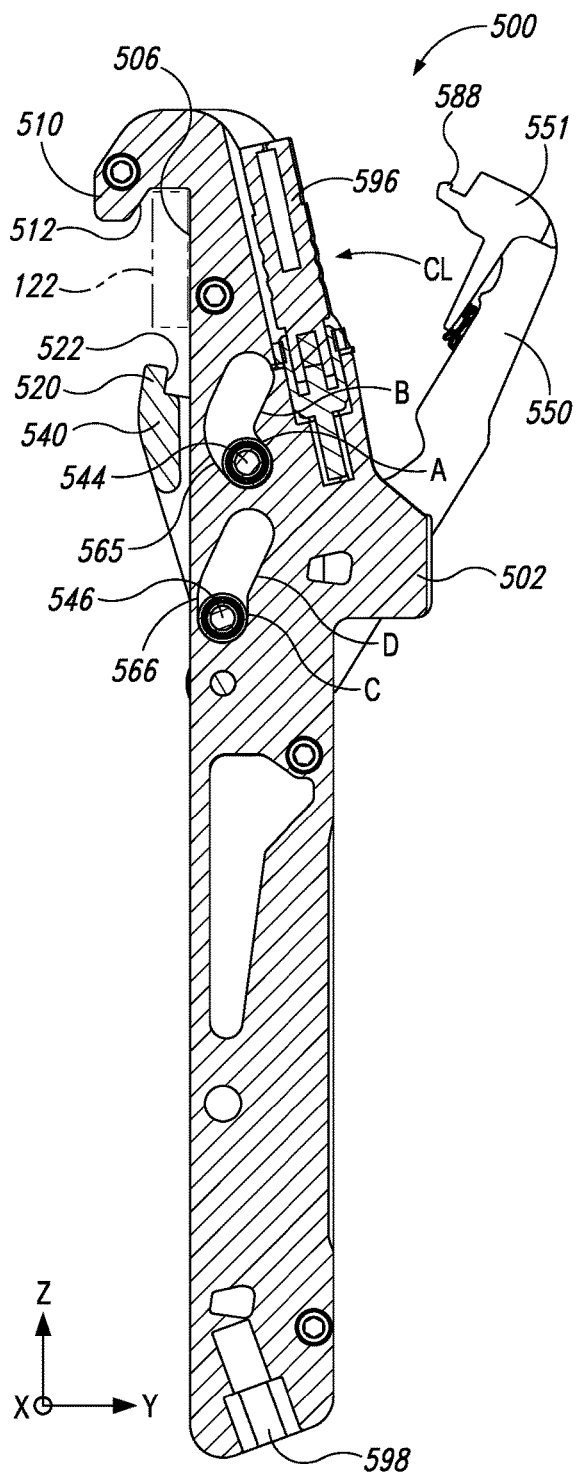
FIGS. 5C-5H are cross-sectional right side views of the modular clamp assembly of FIGS. 5A and 5B, with the cross-sections taken along corresponding positions shown in FIGS. 5A and 5B.
Figure 5D:
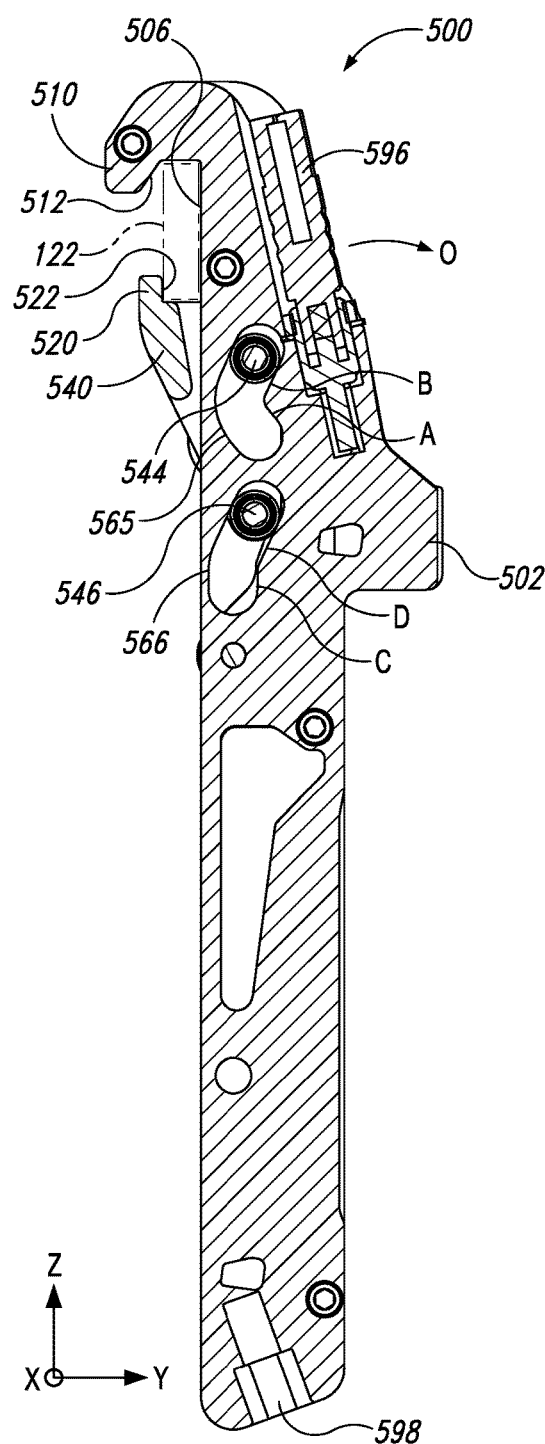
Figure 5E:
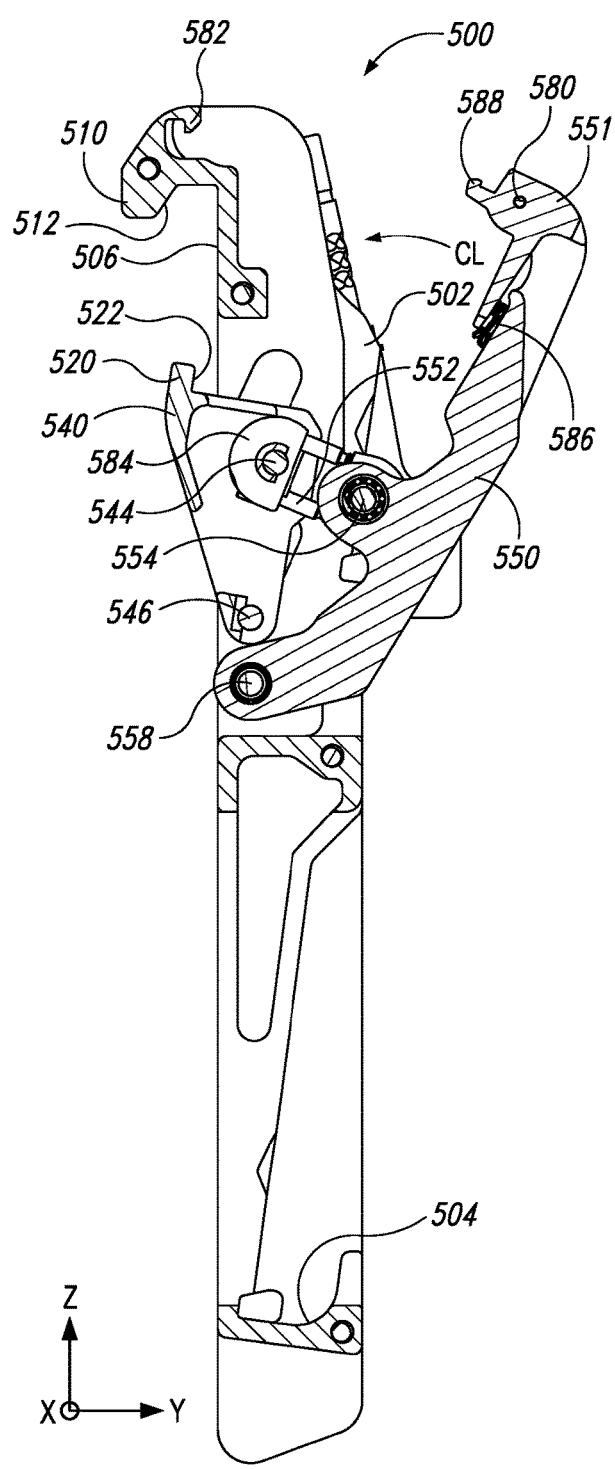
Figure 5F:
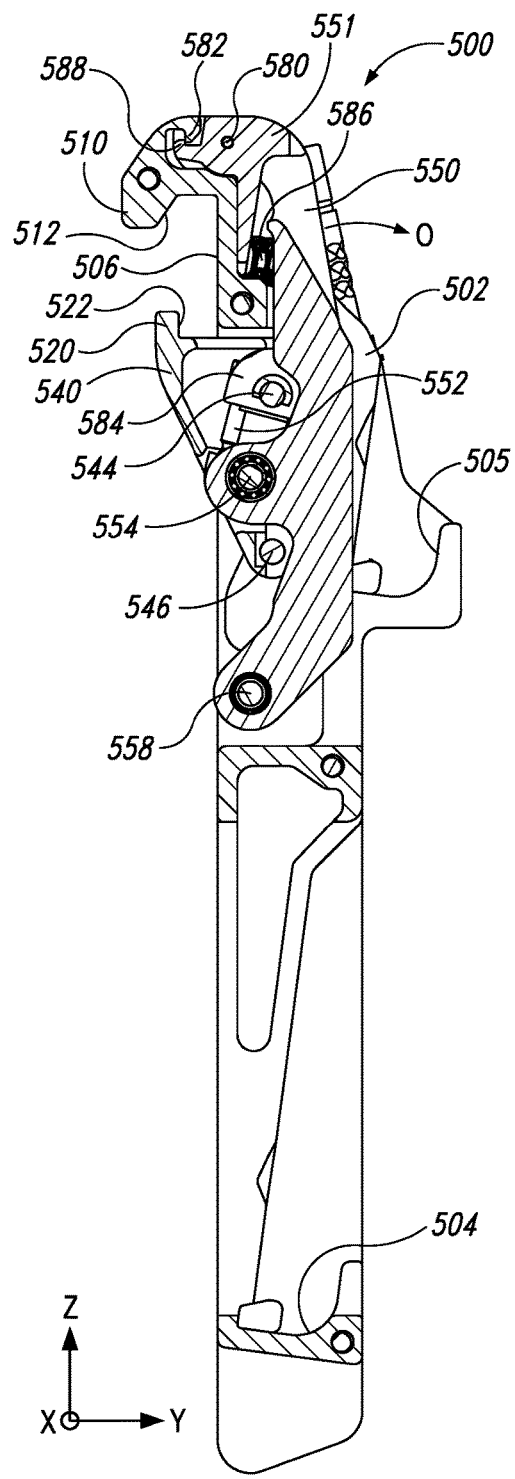

FIGS. 5C-5H show cross-sectional right side views of the clamp 500, the cross-sections taken along corresponding positions shown in FIGS. 5A and 5B. In some embodiments, the clamping articulation of the clamp 500 is accomplished by rotating the lever 550 (compare FIGS. 5C, 5E, and 5G with 5D, 5F, and 5H, respectively) that moves the articulable bracket 540 to draw the jaws 510 and 520 together to clamp the mounting structure 122. Referring initially to FIGS. 5C and 5D, the upper jaw 510 includes the first upper lateral clamping surface 512 that may be configured to abut a portion (e.g., a lateral surface, an upper corner, etc.) of the mounting structure 122 during clamping of the clamp 500. The upper lateral clamping surface 512 may be angled or notched with respect to an opposing surface 506 of the body 502 such that the upper lateral clamping surface 512 can accommodate various widths of the mounting structure 122. In this regard, rails with thinner widths would contact the upper lateral clamping surface 512 at a higher position along the opposing surface 506 than rails with thicker widths, which would contact the rail nearer a tip of the upper jaw 510.

Similarly, the lower jaw 520 may include a lower lateral clamping surface 522. The lower lateral clamping surface 522 may be configured to abut a lower corner of the mounting structure 122 during clamping of the clamp 500. As shown in FIG. 5D, the upper and lower lateral clamping surfaces 512 and 522 may abut one or more of the lateral surface or upper and lower corners of the mounting structure 122, e.g., the corners positioned away from the opposing surface 506 in the clamped position. In contrast to the clamp 200, the clamp 500 may contact the mounting structure 122 on a lateral surface abutting the opposing surface 506 and the upper and lower outer corners and/or the lateral surface of the mounting structure 122 opposite the opposing surface 506. In this regard, the upper and lower lateral clamping surfaces 512 and 522 may capture the mounting structure 122 against the rail opposing surface 506 such that the mounting structure 122 has opposing pressure on both lateral sides when the clamp 500 is clamped.

Referring to FIGS. 5C-5H together, the articulable bracket 540 may be movable by the lever 550 with respect to the body 502. During rotation of the lever 550 in the direction of arrow O, the articulable bracket 540 may be configured to generally follow a segmented arcuate path based on the movement of an upper pin 544 within an upper slot 565 and a lower pin 546 within a lower slot 566. As shown in FIGS. 5C and 5D, the upper slot 565 may have a segmented path with at least a first segment A and a second segment B arranged in different directions, and the lower slot 566 may have a segmented path with at least a third segment C and a fourth segment D arranged in different directions. The first and second segments A and B may be substantially linear, may be any suitable shape (e.g., arcuate), may be combined into a single segment, or may be split into more than two segments to create a suitable path of travel of the articulable bracket 540 during clamping of the clamp 500. Likewise, the third and fourth segments C and D may be substantially linear, may be any suitable shape (e.g., arcuate), may be combined into a single segment, or may be split into more than two segments to create a suitable path of travel of the articulable bracket 540 during clamping of the clamp 500. In the illustrated embodiments, the upper and lower slots 565 and 566 do not have the same length, orientation, or configuration. However, in other embodiments, the upper and lower slots 565 and 566 may have substantially the same length, orientation, and configuration, or any suitable length, orientation, and/or configuration. As shown, the transition between the first and second segments A and B and between the third and fourth segments C and D may have an arcuate shape to smoothly transition the motion of the articulable bracket 540 as the articulable bracket 540 transitions from travel within the second and fourth slots B and D to the first and third slots A and C during clamping of the clamp 500.

As shown in FIGS. 5C and 5D, the upper pin 544 may travel within the upper slot 565 and the lower pin 546 may travel within the lower slot 566 during movement of the articulable bracket 540. Referring initially to the position of the articulable bracket 540 in FIG. 5C, the upper pin 544 will generally be positioned in the first segment A of the upper slot 565, and the lower pin 546 will generally be positioned in the third segment C of the lower slot 566. As shown, the first segment A is disposed at an angle from the second segment B and the third segment C is disposed at a different angle from the fourth segment D. In other embodiments, the orientation of the first segment A may be any suitable angle with respect to the second segment B, and the orientation of the third segment C may be any suitable angle with respect to the fourth segment D.

The first and third segments A and C may control the travel of the articulable bracket 540 from the unclamped position (FIG. 5C) as the clamp 500 articulates to the clamped position (FIG. 5D). The orientation of the first segment A has a directional component in the horizontal Y-direction and a directional component in the vertical Z-direction. Such an orientation will cause the lower jaw 520 to translate substantially outward in the negative Y-direction away from the opposing surface 506, clearing the bottom surface of the mounting structure 122, and travel upward in the Z-direction. The orientation of the third segment C has a directional component in the vertical Z-direction. Such an orientation will allow the articulable bracket 540 to translate substantially upward in the Z-direction as the lower jaw 520 rotates outward in the negative Y-direction.

As the upper pin 544 and the lower pin 546 transition from the first and third segments A and C to the second and fourth segments B and D, at the same or different times, the direction of travel of the articulable bracket 540 will change based on the orientation of the second and fourth segments B and D. In this regard, the orientation of the second segment B has a directional component in the horizontal Y-direction and a directional component in the vertical Z-direction. The orientation of the fourth segment D has a directional component in the horizontal Y-direction and a directional component in the vertical Z-direction. Such an orientation will cause the lower jaw 520 to continue to translate substantially upward in the Z-direction, toward the bottom surface of the mounting structure 122, and the articulable bracket 540 to move in the Y-direction such that the lower lateral clamping surface 522 translates toward the lateral surface of the mounting structure 122.

As shown in the unclamped position of FIG. 5C, when the upper pin 544 is in the furthest position within the first segment A away from the opposing surface 506 and the lower pin 546 is also in the lowest position within the third segment C away from the opposing surface 506, the lower jaw 520 may generally be positioned immediately adjacent to or abutting the body 502. In this regard, it is possible to retract the articulable bracket 540 such that the lower jaw 520 minimally protrudes away from the body 502, which may aid in attaching the clamp 500 to the mounting structure 122 prior to clamping. In other embodiments, the body 502 may have an indentation (not shown) configured to receive the lower jaw 520 (see e.g., the indentation 308 in FIG. 3C) such that the lower jaw 520 may be positioned to not protrude from the body 502. As described above, the lever 550 may be used to transition the clamp 500 between the clamped and unclamped positions by pivoting the lever 550 about a pivot 558 away from the body 502 in the direction of arrow O. As the lever 550 is pivoted away from the body 502, a lever pin 554 begins to generally translate in the Y-direction, and eventually allows the articulable bracket 540 to move from the position in FIG. 5D (clamped) to the position in FIG. 5C (unclamped). The lever pin 554 may use an over-center locking design, as will be explained in greater detail below with respect to FIGS. 5G and 5H.

With reference to FIGS. 5C-5H, the movement of the components of the clamp 500 during one representative embodiment of clamping to a mounting structure 122 will now be described in greater detail. Initially referring to the unclamped state shown in FIG. 5C, the clamp 500 will initially be placed on the mounting structure 122 by interfacing the upper jaw 510 with the mounting structure 122. In this configuration, the opposing surface 506 will contact the lateral surface of the mounting structure 122 facing the opposing surface 506, and the upper lateral clamping surface 512 will contact an upper corner of the mounting structure 122.

When the lever 550 is rotated in the direction of arrow CL (e.g., from FIG. 5C to 5D), the lever pin 554 is pivoted with the lever 550 about the pivot 558, and may therefore cause the lower jaw 520 to follow an arcuate path away from the opposing surface 506. The lever pin 554 may be operably coupled to a translating junction 584 through a telescoping piston assembly 552 configured to extend and retract such that the lever pin 554 and the translating junction 584 are movable with respect to each other during clamping of the clamp 500. The translating junction 584 may be coupled to the upper pin 544 such that the translating junction 584 travels along the path of the upper slot 565 through the movement of the lever 550. The telescoping piston assembly 552 may be dampened and/or biased (e.g., with a biasing member 532 (see FIGS. 5G and 5H) surrounding the telescoping piston assembly 552) such that movement of the lever pin 554 with respect to the translating junction 584 is restricted.

Figures 5G, 5H:
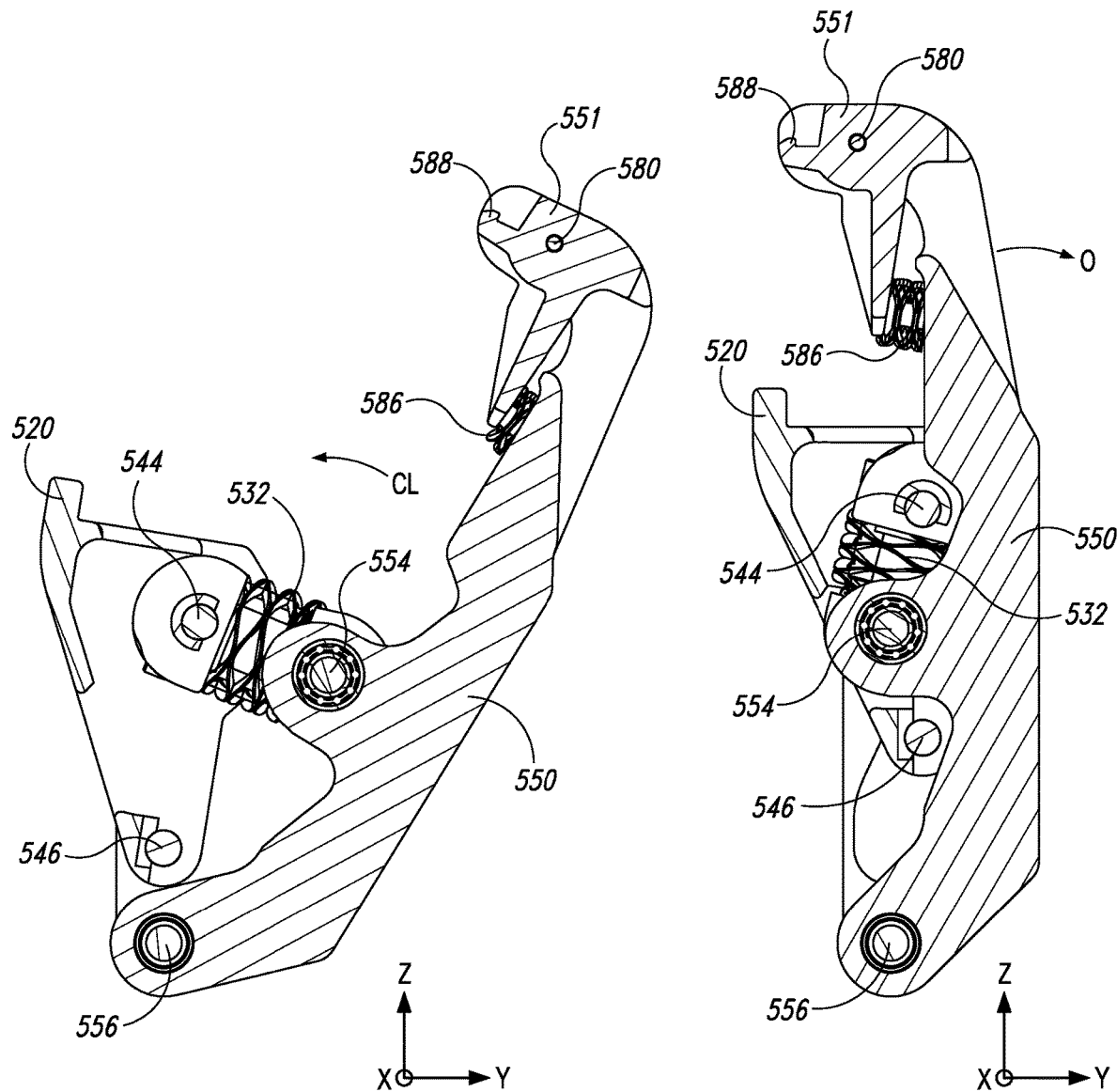

The damping and/or biasing of the telescoping piston assembly 552 may aid in clamping of the clamp 500 onto the mounting structure 122 and provide a force to hold the lever 550 against the body 502 in the clamped position using the over-center configuration shown in FIG. 5H. As shown, when the lever 550 is in the closed/clamped position the lever pin 554 is positioned closer to the opposing surface 506 in the Y-direction than a straight line connecting the lever pivot 558 and the upper pin 544. In this regard, the biasing member 532 exerts a force tending the separate the translating junction 585 from the lever pin 554, and as a result of the position of the lever pin 554 in the over-center configuration, the lever 550 is biased toward the closed position until the lever 550 is rotated in the direction of arrow O such that the lever pin 554 is positioned further from the opposing surface 506 and the Y-direction than a straight line connecting the lever pivot 558 and the upper pin 544. To aid in retention of the lever 550 in the closed position, as shown in FIGS. 5G and 5H, the handle portion 551 may be configured to articulate about a pivot 580 and have a detent tooth 582 configured to interface with a detent tooth 588 (see FIGS. 5E and 5F) of the body 502. The articulation of the handle portion 551 may be biased to a locked position, engaging the detent teeth 582 and 588, by a biasing member 586. As the clamp 500 is transition from the clamped position to the unclamped position, the handle portion 551 would first be articulated about the pivot 580, compressing the biasing member 586, to release the detent teeth 582 and 588, then the lever 550 would be rotatable with respect to the body 502. In other embodiments, the lever 550 may have a manual lock or other suitable retention feature to keep the clamp 500 in the clamped position until removal.

In embodiments of the clamp 500, certain of the components (e.g., the upper and lower slots 565 and 566, the pins 544 and 546, the telescoping piston assembly 552, etc.) may be positioned on either side of the clamp 500 in the X-direction (e.g., in pairs), such that a plurality of these components are used to articulate the clamp 500 during clamping to the mounting structure 122. In other embodiments, components illustrated as having two or more instances, may be used with a single instance, or more instances than illustrated herein, and are within the scope of the present disclosure.

As also shown in FIG. 5C, in the unclamped position, the articulable bracket 540 is positioned downward away from the mounting structure 122. In this configuration, the opening between the upper and lower jaws 510 and 520 may be maximized, and the lower jaw 520 may be adjacent to the body 502 or optionally retracted within an indentation to allow ingress of the mounting structure 122 between the upper and lower jaws 510 and 520. As the lever 550 rotates in a direction of arrow CL, the translating junction 585 and the upper pin 544 travel along the first segment A toward the second segment B and the lower pin 546 travels along the third segment C toward the fourth segment D to substantially translate the articulable bracket 540 in the direction of the first and third segments A and C.

For an initial portion of such movement, the lower jaw 520 translates in the negative Y-direction away from the body 502 and upward in the Z-direction toward the mounting structure 122. At the transition point where the upper pin 544 reaches the second segment B of the upper slot 565 and the lower pin 546 reaches the fourth segment D of the lower slot 566, the direction of translation of the articulable bracket 540 will transition to translation in the Z-direction toward the bottom surface of the mounting structure 122 with a component laterally inward in the Y-direction toward the lateral surface of the mounting structure 122. As the articulable bracket 540 continues upward along the path of the second and fourth segments B and D. When the lower jaw 520 contacts the bottom surface of the mounting structure 122, the lower lateral clamping surface 522 may not yet be in contact with the lateral surface of the mounting structure 122 four clamping of the clamp 500. As described above, the movement of the translating junction 584 with respect to the lever pin 554 may be biased by the biasing member 532. As the lever 550 continues to be rotated to the closed position, the articulable bracket 540 will no longer move upward in the Z-direction and further upward movement of the lever pin 554 will compress the biasing member 532. This continued movement will only have a component in the Y-direction drawing the lower lateral clamping surface 522 toward the lateral surface of the mounting structure 122.

After further rotation of the lever 550, the lower lateral clamping surface 522 will abut the lateral surface of the mounting structure 122, as shown in FIG. 5D. When the lower jaw 520 and the lower lateral clamping surface 522 are in contact with the mounting structure 122, the lower jaw 520 will no longer move with respect to the mounting structure 122, and the biasing member 532 may continue to compress as the lever 550 is rotated to the closed position abutting the body 502 and the detent teeth 582 and 588 catch. The clamp 500 may be removed from the mounting structure 122 by rotating the lever 550 in the direction of arrow O (see FIGS. 5D, 5F, and 5H), in which the movement of the components of the clamp 500 described above will be substantially reversed.

The clamps 200, 300, 400, and 500 described above may include various sensors (not shown) to transmit data signals regarding aspects of the clamp. Embodiments of the present disclosure may include one or more of the following: (1) strain gauges and/or load sensors to indicate an improper coupling and/or load on the clamp; (2) surface acoustic wave sensors (SAW) to determine residence related to security of the clamp on the rail; (3) an inductive coil for metal proximity; (4) a mechanical grounding sensor; (5) a mutual clamp proximity sensor (e.g., line of sight, laser rangefinder, LIDAR, etc.); (6) a rail orientation sensor, table angle sensor, and/or rail twist sensor (e.g., clamp-to-clamp, bending underload and/or oscillation, etc.); and (7) a user touch sensor to prevent an invalid state of the clamp. The clamps 200, 300, 400, and 500 may also include various illumination features (not shown) to indicate certain aspects of the clamp, e.g., a locked state of the clamp, and unlock stated the clamp, overloading of the clamp, etc.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present disclosure. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A system, comprising:
a surgical manipulator configured to control motion of a surgical tool; and
a clamping apparatus having a mounting location configured to support the surgical manipulator and couple to a mounting structure, the clamping apparatus comprising:
a body;
a first jaw coupled to the body and configured to engage a first portion of the mounting structure; and
a second jaw coupled to the body and configured to engage a second portion of the mounting structure,
wherein at least one of the first jaw and the second jaw is movably coupled to the body and configured to move along a path from an unclamping position to one of a range of a clamping positions placing the clamping apparatus in a clamped mechanical state to clamp mounting structures of different sizes,
wherein the path comprises:
a first segment in which the at least one of the first jaw and the second jaw translates relative to the body in a direction away from the body and toward the other of the at least one of the first jaw and the second jaw, and
a second segment in which the at least one of the first jaw and the second jaw translates relative to the body in a direction toward the body and toward the other of the at least one of the first jaw and the second jaw.

2. The system of claim 1, wherein the non-linear path is arcuate.

3. The system of claim 1, wherein the mounting structure comprises a rail, and wherein the first jaw is configured to abut an upper portion of the rail and the second jaw is configured to abut a lower portion of the rail when the clamping apparatus is in the clamped mechanical state.

4. The system of claim 1, wherein at least one of the first jaw and the second jaw has an angled surface to accommodate a range of widths of the mounting structure.

5. The system of claim 1, wherein the body further comprises a mounting feature configured to receive a component and releasably couple the component to the clamping apparatus.

6. The system of claim 1, further comprising a sensor configured to detect load on the clamping apparatus and signal an improper connection.

7. The system of claim 1, wherein:
the first segment of the path has a larger directional component away from the body than toward the other of the at least one of the first jaw and the second jaw, and the second segment of the path has a smaller directional component toward the body than toward the other of the at least one of the first jaw and the second jaw.

8. The system of claim 1, wherein:
the body further comprises a first cam slot and a second cam slot,
the first jaw is fixed to the body, and
the second jaw is movably coupled to the body via pins movable within the first and second cam slots.

9. The system of claim 8, further comprising:
a lever pivotably coupled to the body and the second jaw, the lever movable between (a) a first position wherein the second jaw is in the unclamping position and the clamping apparatus is in an unclamped mechanical state, and (b) a second position wherein the second jaw in in the clamping position and the clamping apparatus is in the clamped mechanical state; and
a biasing member positioned between the body and the lever and configured to bias the second jaw against the mounting structure in the first position.

10. The system of claim 9, wherein
articulation of the lever from the first position toward the second position causes the pins to move within the first and second cam slots to move
the second jaw along the first segment of the path, and
further articulation of the lever toward the second position, in a state of the second jaw contacting the mounting structure causes the biasing member to compress along a compliance direction.

11. The system of claim 10, wherein movement of the second jaw in response to movement of the pins within the first and second cam slots is locked when the lever is in the second position.

12. The system of claim 11, wherein movement of the pins within the first and second cam slots is locked by a toothed interface between the lever and the body, fixing the biasing member in the compliance direction.

13. The system of claim 9, wherein
the biasing member is a first biasing member and the compliance direction is a first compliance direction,
the clamping apparatus further comprises an articulable bracket positioned between the second jaw and the body and configured to allow movement of the second jaw in a second compliance direction independent of the movement of the pins within the first and second cam slots, and
the movement of the second jaw with respect to the articulable bracket is biased by a second biasing member.

14. The system of claim 9, wherein the lever is retained in the second position by an over-center configuration.

15. The system of claim 9, wherein the lever has an articulable portion that interfaces with the body to retain the lever in the second position until the articulable portion is rotated.

16. The system of claim 9, wherein:
the biasing member is a first biasing member positioned between the body and
the lever and configured to bias the lever toward the first position,
articulation of the lever toward the second position in a state of the second jaw contacting the mounting structure causes the first biasing member to compress along a first compliance direction, and
the system further comprises a second biasing member positioned between an articulable bracket and the second jaw and configured to bias the second jaw away from the articulable bracket, wherein articulation of the lever toward the second position in a state of the second jaw contacting the mounting structure causes the second biasing member to compress along a second compliance direction.

17. A system, comprising:
a surgical manipulator configured to control motion of a surgical tool; and
a clamping apparatus having a mounting location configured to support the surgical manipulator and couple to a mounting structure, the clamping apparatus comprising:
  a body having a cam slot defining a non-linear path;
  a first jaw coupled to the body and configured to engage a first portion of the mounting structure; and
  a second jaw movably coupled to the body via a pin engaged in the cam slot, the second jaw configured to engage a second portion of the mounting structure,
wherein the second jaw is configured to move along a non-linear path between and unclamping position and a clamping position in response to movement of the pin along the cam slot.

18. The system of claim 17, further comprising:
a lever pivotably coupled to the body and the second jaw, the lever movable between (a) a first position wherein the second jaw is in the unclamping position and the clamping apparatus is in an unclamped mechanical state, and (b) a second position wherein the second jaw in in the clamping position and the clamping apparatus is in a clamped mechanical state; and
a biasing member positioned between the body and the lever and configured to bias the second jaw against the mounting structure in the first position.

19. The system of claim 18, wherein
articulation of the lever from the first position toward the second position causes the pin to move within the cam slot to move the second jaw along the non-linear path, and
further articulation of the lever toward the second position, in a state of the second jaw contacting the mounting structure causes the biasing member to compress along a compliance direction.

20. The system of claim 19, wherein movement of the second jaw in response to movement of the pin within the cam slot is locked when the lever is in the second position.

21. The system of claim 18, wherein:
the biasing member is a first biasing member and the compliance direction is a first compliance direction,
the clamping apparatus further comprises an articulable bracket positioned between the second jaw and the body and configured to allow movement of the second jaw in a second compliance direction independent of the movement of the pin within the cam slot, and
the movement of the second jaw with respect to the articulable bracket is biased by a second biasing member.

22. The system of claim 18, wherein the lever is retained in the second position by an over-center configuration.

* * * * *

UNITED STATES PATENT AND TRADEMARK OFFICE
CERTIFICATE OF CORRECTION

| | | |
|---|---|---|
| PATENT NO. | : 12,285,301 B2 | Page 1 of 1 |
| APPLICATION NO. | : 17/444158 | |
| DATED | : April 29, 2025 | |
| INVENTOR(S) | : Ryan C. Abbott, Daniel H. Gomez and John Ryan Steger | |

It is certified that error appears in the above-identified patent and that said Letters Patent is hereby corrected as shown below:

In the Claims

In Claim 2 at Column 35, Line 46, delete "non-linear".

Signed and Sealed this
Thirtieth Day of September, 2025

John A. Squires
*Director of the United States Patent and Trademark Office*